United States Patent
Sano et al.

(10) Patent No.: US 6,589,967 B1
(45) Date of Patent: Jul. 8, 2003

(54) OXIME O-ETHER COMPOUNDS AND FUNGICIDES FOR AGRICULTURAL AND HORTICULTURAL USE

(75) Inventors: Hiroshi Sano, Kanagawa (JP); Tadashi Sugiura, Kanagawa (JP); Yuuki Nakagawa, Gainesville, FL (US); Hiroshi Hamamura, Shizuoka (JP); Akira Mitani, Kanagawa (JP); Takahiro Ando, Kanagawa (JP)

(73) Assignee: Nippon Soda Co. Ltd., Tokyo (JP)

( * ) Notice: Subject to any disclaimer, the term of this patent is extended or adjusted under 35 U.S.C. 154(b) by 0 days.

(21) Appl. No.: 10/129,646

(22) PCT Filed: Nov. 2, 2000

(86) PCT No.: PCT/JP00/07744

§ 371 (c)(1), (2), (4) Date: May 6, 2002

(87) PCT Pub. No.: WO01/34568

PCT Pub. Date: May 17, 2001

(30) Foreign Application Priority Data

Nov. 5, 1999 (JP) .............................. 11-314544
Mar. 31, 2000 (JP) ........................ 2000-096516

(51) Int. Cl.[7] ...................... A01N 43/40; C07D 213/53; C07D 213/44
(52) U.S. Cl. ........................ 514/345; 514/348; 514/349; 514/351; 514/352; 514/357; 546/290; 546/296; 546/297; 546/300; 546/304; 546/307; 546/311; 546/312; 546/338
(58) Field of Search ................... 548/290, 296, 548/297, 300, 304, 307, 311, 310, 338; 514/345, 348, 349, 351, 352, 357

(56) References Cited

U.S. PATENT DOCUMENTS

| | | | |
|---|---|---|---|
| 5,055,471 A | 10/1991 | de Frainer et al. | |
| 5,965,613 A | 10/1999 | Isenring et al. | |

FOREIGN PATENT DOCUMENTS

| | | |
|---|---|---|
| DE | 4213149 | 10/1993 |
| EP | 0004754 | 10/1979 |
| EP | 0024888 | 3/1981 |
| JP | 05-051364 | 2/1993 |
| JP | 07-196617 | 1/1995 |
| JP | 09-003047 | 7/1997 |
| WO | WO 93/21157 | 10/1993 |

*Primary Examiner*—Patricia L. Morris
(74) *Attorney, Agent, or Firm*—Dennis G. LaPointe

(57) ABSTRACT

The present invention relates to novel oxime O-ether compounds represented by a general formula [I];

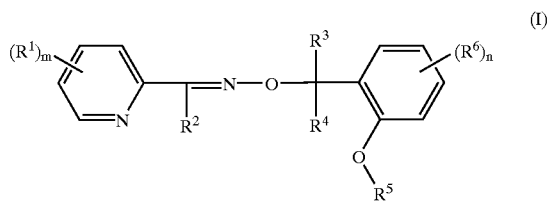

wherein $R^1$ represents $C_{1-6}$ alkyl, $C_{3-6}$ cycloalkyl, $C_{1-6}$ alkoxy, etc., m represents an integer of 1 to 4, $R^2$ represents hydrogen atom, $C_{1-6}$ alkyl, etc., $R^3$ and $R^4$ each independently represents hydrogen atom or $C_{1-6}$ alkyl, etc., $R^5$ represents hydrogen atom, $C_{1-6}$ alkyl, etc., $R^6$ represents $C_{1-6}$ alkyl, $C_{2-6}$ alkenyl, $C_{2-6}$ alkynyl, $C_{1-6}$ alkoxy, Halogen atom, etc. and n represents an integer of 1 to 4, and a fungicide for agricultural and horticultural use comprising the compound as the active ingredient.

4 Claims, No Drawings

OXIME O-ETHER COMPOUNDS AND FUNGICIDES FOR AGRICULTURAL AND HORTICULTURAL USE

FIELD OF INVENTION

The present invention relates to novel oxime O-ether compounds and fungicides containing said compound as an active principle for agricultural and horticultural use.

BACKGROUND ART

For agricultural and horticultural crop culture, various agricultural plant protection chemicals have been used for controlling plant diseases. However, due to deterioration of plant protection chemicals in their activity and the appearance of resistant stains of plant pathogenic microorganisms to those chemicals, the use of fungicides plant protection use has been restricted. In addition, many fungicides cause phytotoxicity to plants or are toxic to humans and animals. Consequently, although there are many fungicides for plant protection use have been developed and used, most of them are not satisfactory in view of said disadvantages. As a result, there is a need yet to provide fungicides for plant protection use, which do not have the above-described disadvantages and can be used safely.

For example, oxime O-ether compounds similar to the compounds as defined in the present invention are disclosed in EP4754, EP24888, WO93/21157 as compounds having insecticidal and acaricidal activity.

Furthermore, it is disclosed in Jpn. Pat. Appln. Publication (KOKAI) No. 9-3047 that oxime O-ether compounds represent by the following chemical formula are useful as a fungicide.

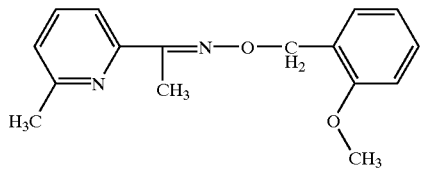

DISCLOSURE OF THE INVENTION

It is an object of the present invention to provide novel oxime O-ether compounds, those which can be an excellent fungicide for agricultural and horticultural use, advantageous for the production in an industrial scale, having firm biological effectiveness, and causing less phytotoxicity.

The inventors of the present invention found that the fungicidal activity of said oxime O-ether compounds represented by the following general formula [I] can be enhanced and phytotoxicity caused thereby can be reduced by introducing an oxygen functional group into the 2nd position of the benzene ring of said oxime O-ether compound and a substituent into an arbitrary position, particularly the 6th position of the benzene ring.

Therefore, the present invention is directed to oxime O-ether compounds represented by a general formula [I];

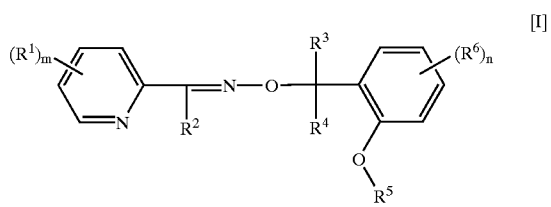

wherein $R^1$ represents $C_{1-6}$ alkyl, $C_{3-6}$ cycloalkyl, $C_{1-6}$ alkoxy, $C_{1-6}$ alkylthio, amino, mono- or di-($C_{1-6}$ alkyl)amino, $C_{1-6}$ acyloxy, $C_{1-6}$ alkoxy $C_{1-6}$ alkyl, $C_{1-6}$ haloalkyl, hydroxy or Halogen atom;

m represents an integer of 1 to 4, and when m is 2 or more integer, each of $R^1$ may be same or different from one to another;

$R^2$ represents hydrogen atom, $C_{1-6}$ alkyl or $C_{3-6}$ cycloalkyl;

$R^3$ and $R^4$ are same or different from one to another and each independently represents hydrogen atom or $C_{1-6}$ alkyl;

$R^5$ represents hydrogen atom, $C_{1-6}$ alkyl, $C_{3-6}$ cycloalkyl, $C_{1-6}$ haloalkyl, $C_{1-6}$ alkoxy $C_{1-6}$ alkyl, $C_{1-6}$ alkoxy $C_{1-6}$ alkoxy $C_{1-6}$ alkyl, $C_{7-10}$ aralkyl, $C_{7-10}$ aralkyloxy $C_{1-6}$ alkyl, $C_{1-6}$ alkylcarbonyl, $C_{1-6}$ alkylsulfonyl or $C_{1-6}$ haloalkylsulfonyl;

$R^6$ represents $C_{1-6}$ alkyl, $C_{3-6}$ cycloalkyl, $C_{2-6}$ alkenyl, $C_{2-6}$ alkynyl, $C_{1-6}$ alkoxy, $C_{1-6}$ alkoxy $C_{1-6}$ alkoxy, $C_{1-6}$ alkylcarbonyloxy, $C_{1-6}$ alkoxy $C_{1-6}$ alkyl, $C_{1-6}$ haloalkyl, cyano, nitro, amino, mono- or di-($C_{1-6}$ alkyl) amino, $C_{1-6}$ alkylcarbonylamino, $C_{1-6}$ alkylthio, hydroxy or Halogeno atom; and n represents an integer of 1 to 4, and when n is 2 or more integer, each of $R^6$ may be same or different from one to another, and fungicides for agricultural and horticultural use containing the oxime O-ether compound or a salt thereof as the active ingredient.

More specifically, in the general formula [I], $R^1$ represents $C_{1-6}$ alkyl, such as methyl, ethyl, propyl, isopropyl, butyl, sec-butyl, isobutyl, t-butyl, pentyl and its isomers, and hexyl and its isomers, an optionally-substituted $C_{3-6}$ cycloalkyl, such as cyclopropyl, cyclopentyl, 1-methylcyclopentyl, cyclohexyl, and 1-methylcyclohexyl, $C_{1-6}$ alkoxy, such as methoxy, ethoxy, propoxy, isopropoxy, butoxy, sec-butoxy, isobutoxy, and t-butoxy, $C_{1-6}$ alkylthio, such as methylthio, ethylthio, isopropylthio, and butylthio, amino, mono- or di-($C_{1-6}$ alkyl)amino, ethylamino, propylamino, dimethylamino, diethylamino, dipropylamino, dibutylamino, and ethylisopropylamino, $C_{1-6}$ acyloxy, such as acetoxy, and propionyloxy, pivaloyloxy, $C_{1-6}$ alkoxy $C_{1-6}$ alkyl, such as methoxymethyl, methoxyethyl, ethoxymethyl, propoxymethyl, and butoxymethyl;

$C_{1-6}$ haloalkyl, such as chloromethyl, fluoromethyl, bromomethyl, dichloromethyl, difluoromethyl, dibromomethyl, trichloromethyl, trifluoromethyl, tribromomethyl, trichloroethyl, trifluoroethyl, and pentafluoroethyl;

hydroxy, or

Halogeno atom atom atom, such as fluorine, chlorine bromine and iodine;

m represents an integer of 1 to 4, and when m is 2 or more integer, each of $R^1$ may be same or different from one another;

$R^2$ represents hydrogen atom, $C_{1-6}$ alkyl, such as methyl, ethyl, propyl, isopropyl, butyl, sec-butyl, isobutyl, t-butyl, pentyl and its isomers, and hexyl and its isomers, or an optionally-substituted $C_{3-6}$ cycloalkyl, such as cyclopropyl, cyclopentyl, 1-methylcyclopentyl, cyclohexy, and 1-methylcyclohexyl;

$R^3$ and $R^4$ may be same or different from one to another and each independently represents hydrogen atom, or $C_{1-6}$ alkyl, such as methyl, ethyl, propyl, isopropyl, butyl, sec-butyl, isobutyl, t-butyl, pentyl and its isomers, and hexyl and its isomers;

$R^5$ represents hydrogen atom, $C_{1-6}$ alkyl, such as methyl, ethyl, propyl, isopropyl, butyl, sec-butyl, isobutyl, t-butyl, pentyl and its isomers, and hexyl and its isomers, an optionally-substituted $C_{3-6}$ cycloalkyl, such as cyclopropyl, cyclopentyl, 1-methylcyclopentyl, cyclohexyl, and 1-methylcyclohexyl, $C_{1-6}$ haloalkyl, such as chloromethyl, fluoromethyl, bromomethyl, dichloromethyl, difluoromethyl, dibromomethyl, trichloromethyl, trifluoromethyl, tribromomethyl, trichloroethyl, trifluoroethyl, and pentafluoroethyl, $C_{1-6}$ alkoxy $C_{1-6}$ alkyl, such as methoxymethyl, methoxyethyl, ethoxymethyl, propoxymethyl, and butoxymethyl, $C_{1-6}$ alkoxy $C_{1-6}$ alkoxy $C_{1-6}$ alkyl, such as methoxyethoxymethyl and ethoxyethoxymethyl, $C_{7-10}$ aralkyl, such as benzyl and phenetyl, $C_{7-10}$ aralkyloxy C1–6 alkyl, such as benzyloxymethyl and benzyloxyethyl, $C_{1-6}$ alkylcarbonyl, such as acetyl, propionyl, and pivaloyl, $C_{1-6}$ alkylsulfonyl, such as methanesulfonyl and ethanesulfonyl, or $C_{1-6}$ haloalkylsulfonyl, such as chloromethylsulfonyl and trifluoromethylsulfonyl;

$R^6$ represents $C_{1-6}$, such as methyl, ethyl, propyl, isopropyl, butyl, sec-butyl, isobutyl, t-butyl, pentyl and its isomers, and hexyl and its isomers, an optionally-substituted $C_{3-6}$ cycloalkyl, such as cyclopropyl, cyclopentyl, 1-methylcyclopentyl, cyclohexyl, and 1-methylcyclohexyl, $C_{2-6}$ alkenyl, such as vinyl, propenyl, and isopropenyl, $C_{2-6}$ alkynyl, such as ethynyl, and propalgyl, $C_{1-6}$ alkoxy, such as methoxy, ethoxy, propoxy, isopropoxy, butoxy, sec-butoxy, isobutoxy and t-butoxy, $C_{1-6}$ alkoxy $C_{1-6}$ alkoxy, such as methoxymethoxy, methoxyethoxy, ethoxymethoxy, propoxymethoxy, and butoxymethoxy, $C_{1-6}$ alkylcarbonyl, such as acetoxy, propionyloxy, and pivaloyloxy, $C_{1-6}$ alkoxy $C_{1-6}$ alkyl, such as methoxymethyl, methoxyethyl, ethoxymethyl, propoxymethyl, and butoxymethyl, $C_{1-6}$ haloalkyl, such as chloromethyl, fluoromethyl, bromomethyl, dichloromethyl, difluoromethyl, dibromomethyl, trichloromethyl, trifluoromethyl, tribromomethyl, trichloroethyl, trifluoroethyl, and pentafluoroehtyl, cyano, nitro, amino, mono- or di-($C_{1-6}$ alkyl)amino, such as methylamino, ethylamino, propylamino, dimethylamino, diethylamino, dipropylamino, dibutylamino, and ethylisopropylamino, $C_{1-6}$ alyklcarbonylamino, such as acetylamino, and, pivaloylamino, $C_{1-6}$ alkylthio, such as methylthio, ethylthio, and isopropylthio, hydroxy, or Halogen atom, such as fluorine, chlorine, bromine and iodine; and n represents an integer of 1 to 4, and when n is 2 or more integer, each of $R^6$ may be same or different from one another.

Of the compounds defined in the present invention, compounds represented by a general formula [I'];

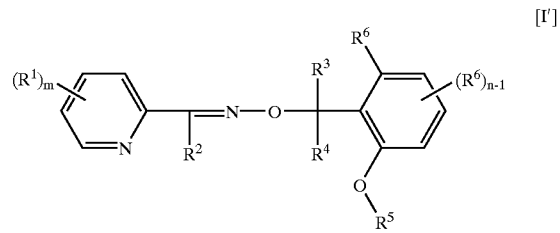

wherein $R^1$, $R^2$, $R^3$, $R^4$, $R^5$, $R^6$, m and n are as defined above, of which benzene ring is substituted by one of the groups exampled above for $R^6$ at the 6th position, have excellent activity as a fungicide for agricultural and horticultural use.

(Fungicide for Agricultural and Horticultural Use)

Each of the compounds defined in the present invention has excellent fungicidal activity against wide range of fungi belonging to, for example, Oomycetes, Ascomycetes, Deuteromycetes and Basidiomycetes. In particular, the compounds of the present invention have remarkable fungicidal activity against a fungus of gray mold disease, *Botrytis cinerae*, compared to the known compounds described above.

The composition containing the compound of the present invention as the active ingredient can be used for controlling various plant diseases infesting on agricultural and horticultural crops including ornamental flowers, lawns and forage crops by means of seed treatment, foliage application soil application, water surface application, etc.

Example of plant diseases those which can be controlled by the application of a composition containing the compound of the present invention include the following.

Sugar beet: Cercospora leaf spot (*Cercospora beticola*)

Groundnut: Leaf spot (*Mycosphaerella arachidis*)
Late leaf spot (*Mycosphaerella berkeleyi*)

Cucumbers: Powdery mildew (*Sphaerotheca fuliginea*)
Gummy stem blight (*Mycosphaerella melonis*)
Sclerotinia rot (*Sclerotinia sclerotiorum*)
Gray mold (*Botrytis cinerea*)
Scab (*Cladosoorium cucumerinum*)

Tomatoes: Gray mold (*Botrytis cinerea*)
Leaf mold (*Cladosporium fulvum*)
Eggplants: Gray mold (*Botrytis cinerea*)
Black rot (*Corynespora melongenea*)
Powdery mildew (*Erysiphe cichoracearum*)
Strawberries: Gray mold (*Botrytis cinerea*) Powdery mildew (*Sphaerotheca aphanis*)
Onion: Gray-mold neck rot (*Botrytis allii*)
Gray-mold (*Botrytis cinerea*)
Kidney bean: Sclerotinia rot (*Sclerotinia sclerotiorum*)
Gray mold (*Botrytis cinerea*)
Apples: Powdery mildew (*Podosphaera leucotricha*)
Scab (*Venturia inaequalis*)
Blossom blight (*Monilinia mali*)
Oriental persimon: Powdery mildew (*Phyllactinia kakicola*)
Anthracnose (*Gloeosporium kaki*)
Angular leaf spot(*Cercospora kaki*)
Peach & Cherries: Brown rot (*Monilinia fructicola*)
Grapes: Gray mold (*Botrytis cinerea*)
Powdery mildew (*Uncinula necator*)
Ripe rot (*Glomerella cingulata*)
Pears: Scab (*Venturia nashicola*)
Rust (*Gymnosporangium asiaticum*)
Black spot (*Alternaria kikuchiana*)
Tea plant: Gray blight(*Pestalotia theae*)
Anthracnose (*Colletotrichum theae-sinensis*)
Citrus: Scab (*Elsinoe fawcetti*)
Blue mold (*Penicillium italicum*)
Common green mold (*Penicillium digitatum*)
Gray mold (*Botrytis cinerea*)
Barley: Powdery mildew (*Erysiphe graminis* f.sp. *hordei*)
Loose smut (*Ustilago nuda*)
Scab (*Gibberella zeae*)
Leaf rust (*Puccinia recondita*)
Spot blotch (*Cochliobolus sativus*)
Eye spot (*Pseudocercosporella herpotrichoides*)
Glume bltch (*Leptosohaeria nodorum*)
Powdery mildew (*Erysiphe graminis* f.sp. *tritici*)
Snow mould (*Micronectriella nivalis*)
Paddy rice: Blast (*Pyricularia oryzae*)
Sheath blight (*Rhizoctonia solani*)
Bakanae disease (*Gibberella fujikuroi*)
Helminthosporium leaf spot (*Cochliobolus miyabeanus*)
Tobacco: Sclerotinia rot (*Sclerotinia sclerotiorum*)
Powdery mildew (*Erysiphe cichoracearum*)
Tulip: Garymold (*Botrytis cinerea*)
Bent grass: Sclerotinia snow blight (*Sclerotinia borealis*)
Orchard grass: Powdery mildew (*Erysiphe graminis*)
Soybean: Purple speck (*Cercospora kikuchii*)
Potatoes & Tomatoes: Downy mildew (*Phytophthora infestans*)
Cucumbers: Downy mildew (*Pseudoperonospora cubensis*)
Grape: Downy mildew (*Plasmopara viticola*)

Besides, in recent years, it should be noted that various plant pathogenic fungi have developed resistance to plant protection chemicals, such as benzimidazole fungicides and carbodiimide fungicides. It follows that there is a problem in the control of such a problematic plant disease, because no fungicide can control those plant diseases sufficiently.

Therefore, an effective fungicide, which can control such fungi being resistant against those problematic plant diseases is badly desired. The compounds of the present invention are effective to those resistant strains of fungi to aforementioned fungicides as well as susceptible ones.

The compounds of the present invention are effective to not only the susceptible fungi but also the resistant strains of fungi including gray mold fungus (*Botrytis cinerea*), sugar beet leaf spot fungus (*Cercospora beticola*), apple scab fungus (*Venturia inaequalis*), and pear scab fungus (*Venturia nashicola*) to, for examples, thiophanate methyl, benomyl and carbendazim.

In addition, the compounds defined in the present invention are also effective against gray mold diseases caused by *Botrytis cinerea* which are resistant to dicarboxyimide fungicides, such as vinclozolin, procymidone and iprodione. The fungicidal activity against the resistant strains of gray mold fungus of the compounds of the present invention is as effective as that against the susceptible strains.

Specifically, examples of plant diseases to those which a fungicidal composition (fungicide for agricultural and horticultural use) containing the compound of the present invention is used more preferably are Cercospora leaf spot of sugar beet, powdery mildew of wheat, blast of paddy rice, scab of apples, gray mold of Kidney bean, leaf spot of groundnut and so on.

Furthermore, the compounds of the present invention can also be used as an antifouling agent for preventing structures in water, such as the bottoms of ships and fishing nets, from fouling of aqueous life.

EMBODIMENTS

The compounds according to the present invention are produced according to a process represent by the following reaction equation; 1)

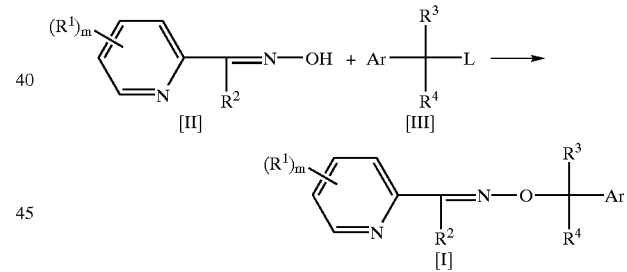

wherein $R^1$, $R^2$, $R^3$, $R^4$ and m are as defined above, Ar represents a substituted phenyl group represented by a formula;

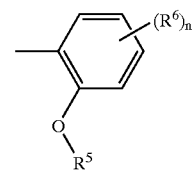

wherein $R^5$, $R^6$ and n are as defined above, and L represents Halogen atom, such as chlorine, bromine and iodine, or an eliminating group, such as methanesulfonyloxy and p-toluenesulfonyloxy.

Specifically, in the reaction equation (1) given above, the compounds represented by the general formula [I] can be produced by allowing a compound of the formula [II] and a compound of the formula [III] to react with each other without solvent or preferably in a solvent while stirring for 10 min. to 24 hours at a reaction temperature of 0 to 150° C. and in the presence of a deacidifying agent.

Examples of the solvent to be used in the above reaction (1) include a ketone, such as acetone and 2-butanone, an ether, such as diethyl ether and tetrahydrofuran, an aromatic hydrocarbon, such as benzene and toluene, an alcohol, such as methanol and ethanol, acetonitrile, N,N-dimethylformamide, dimethylsulfoxide and water. One or more solvents recited above can be used in combination for the reaction.

Examples of the base to be used in the above reaction (1) include an inorganic base, such as sodium hydroxide, potassium hydroxide, sodium carbonate and sodium hydride, an alkali metal alcolate, such as sodium methylate and sodium ethylate, and an organic base, such as pyridine, triethylamine and DBU.

The stating material represented by the formula [II] for producing the compounds according to the present invention can be produced according to the process disclosed in Jap. Pat. Appln. KOKAI Publication No. 9-3047. 2)

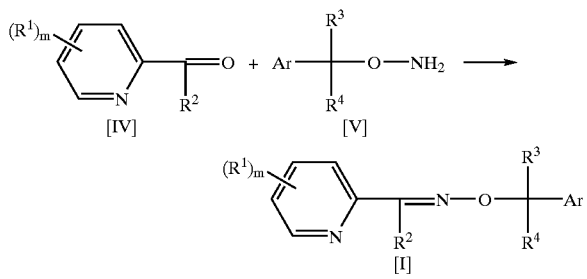

wherein $R^1$, $R^2$, $R^3$, $R^4$, Ar and m are as defined above.

Specifically, in the reaction equation (2) given above, the compound represented by the general formula [I] is produced by allowing a compound resented by the formula [IV] and a compound represented by the formula [V] or a salt thereof to react with each other while stirring without solvent or preferably in a solvent for a period of from 10 min. to 24 hours at a reaction temperature in a range of from 0 to 150° C.

Example of the solvent to be used in the above reaction (2) include an alcohol, such as ethanol and methanol, an ether, such as diethyl ether, tetrahydrofuran and dioxane, a cellosolve, such as methyl cellosolve and ethyl cellosolve, an aromatic hydrocarbon, such as benzene and toluene, acetic acid, N,N-dimethylformamide, dimethylsulfoxide, and water. One or more solvents recited above can also be used in combination for the reaction (2). The reaction (2) does not require the presence of a catalyst, however, the reaction may be accelerated by an addition of an acid or a base sometime. Examples of the catalytic acid include an inorganic acid, such as sulfuric acid and hydrochloric acid, and an organic acid, such as p-toluene sulfonic acid. Examples of the catalytic base include acetic acid and the like.

Following to the completion of the reactions (1) and (2), the targeted compounds can be obtained by subjecting the reaction products to common post-reaction processing. Note that the obtained targeted compounds can be further chemically modified to produce various derivatives thereof. More specifically, as said chemical modification, functional group conversion represented by induction of nitro group to amino group by reduction reaction, deblocking of functional groups, such as methoxymethyl group, recognized in the organic chemistry field as a protecting group, induction of functional groups, such as hydroxy group and amino group, generated by the deblocking by means of alkylation and acylation, and induction of functional groups, represented by Sonogashira reaction, recognized as a deblocking group in the organic chemistry field, such halogenatoms, with use of a nucleophilic reagent are exemplified.

Said salts of the compound of the formula [I] can be produced by performing a reaction of the compound of the formula [I] and either an inorganic acid or an organic acid in an appropriate solvent.

The chemical structures of the compounds according to the present invention are determined by use of NMR, mass spectrum, and so on.

[Fungicide]

The fungicide according to the present invention contains one or more of the compounds defined in the present invention as the active ingredient. In the practical application of the compounds of the present invention, the compounds can be used in a form of the pure compound without combining other component thereto. As well, the compound of the present invention can be prepared in a common formulation form to be used for the purpose of an plant protection chemical, for example, wettable powder, granules, powder, emulsifiable concentrate, water-soluble formulation, suspension concentrate, flowable and so on.

Examples of additives and carriers to be used in the formulations for plant protection use of the compound of the present invention are as follows. For the solid type formulations, phytogenic powdery materials, such as soybean powder and flours, mineral fine powders, such as diatomaceous earth, apatite, gypsum, talc, bentonite, pyrophyllite and clay, and organic and inorganic compounds, such as sodium benzoate, urea and Glauber's salt.

In case that the compounds of the present invention are prepared to liquid type formulations, petroleum fractions including kerosine, xylene and solvent naphtha, cyclohexane, cyclohexanone, dimethylformamide, dimethylsulfoxide, alcohols, acetone, trichloroethylene, methyl isobutyl ketone, mineral oils, vegetable oils, water, etc. can be used as a solvent.

In addition, in order to provide uniformity and stability to the exampled formulations, it is possible to add surface active agents into each of the formulations upon necessity. Examples of the surface active agent that can be added to said formulations include a nonionic surface active agent, such as polyoxyethylene-added alkyl phenyl ether, polyoxyethylene-added higher fatty acid ester, polyoxyethylene-added sorbitan higher fatty acid ester and polyoxyethylene-added tristyryl phenyl ether, a sulfate ester of polyoxyethylene-added alkyl phenyl ether, an alkyl benzene sulfonate, a sulfate ester of higher alcohol, an alkyl naphthalene sulfonate, a polycarbonate, a lignin sulfonate, a formaldehyde condensate of alkyl naphthalene sulfonate, and a copolymer of isobutylene-maleic anhydride.

In general, the content of an active ingredient in each of the formulations recited above is preferably in a range of from 0.01 to 90% by weight, and more preferably from 0.05 to 85% by weight based on the total weight of the composition (formulation).

Each of the prepared formulations, such as wettable powder, emulsifiable concentrate and flowable concentrate, is diluted with water so as to prepare the diluted solution or the suspension at a desired concentration and is applied to crop plants by, for example, spraying. For the formulations, such as granular and power formulations, the formulation itself is directly applied to the target crop plants. Therefore, the fungicidal composition according to the present invention prepared into the respective formulation types described above is applied to crop plants, seeds, water surface and soil either directly or in a form of diluted solution with water.

Explanation will now be made for the application dose of the respective formulations. The application dose may differ depending on various conditions, such as climatic condition, a type of formulation, the time of application, an application method, whereto apply, the target disease to be controlled, the target crop plant, etc. However, the application dose based on the active ingredient per hectare is normally in a range of from 1 to 1,000 g, and preferably from 10 to 100 g per hectare.

More specifically, where wettable powder, emulsifiable concentrate, suspension concentrate or liquid formulation is applied by dilution with water, the concentration of the active ingredient in the dilution will be in a range of from 1 to 1,000 ppm, and preferably from 10 to 250 ppm. On the other hand, in case of granular and powder formulations, they are directly applied without making the dilution.

Needless to say that the compound alone according to the present invention has sufficient fungicidal activity, however, it can be combined for the use with one or more of various types of other plant protection chemicals, for example, fungicides, insecticides, acaricides and synergists.

Hereunder, representative examples for fungicides, insecticides, acaricides, nematicides and plant growth regulators those which can be combined to use with the fungicidal composition according to the present invention will be recited.

Fungicides

Copper-base fungicides: Basic copper chloride, Basic copper sulfate, etc.

Sulfur-base fungicides: Thiuram, Zineb, Maneb, Mancozeb, Ziram, Propineb, Polycarbamate, etc.

Polyhaloalkylthio-type fungicides: Captan, Folpet, Dichlorfluanid, etc.

Organochloric fungicides: Chlorothalonil, Fthalide, etc.

Organophosphorous fungicides: IBP, EDDP, Triclofos methyl, Pyrazophos, Fosetyl, etc.

Benzimidazol fungicides: Thiophanate methyl, Benomyl, Carbandazim, Thiabendazol, etc.

Dicarboxyimide fungicides: Iprodione, Procymidone, Vinclozolin, Fluorimide, etc.

Carboxyamide fungicides: Oxycarboxine, Mepronil, Flutolanil, Tecloftalam, Trichlamide, Pencycuron, etc.

Acylalanine fungicides: Metalaxyl, Oxadixyl, Fralaxyl, etc.

Methoxyacrylate fungicides: Clethoxime methyl, Azoxystrobine, Methominostrobine, etc.

Anilinopyrimidine fungicides: Andopurine, Mepaniprim, Pyrimethanil, Diprodinyl, etc.

SBI fungicides: Triadimefon, Triadimenol, Bitertanol, Microbutanil, Hexaconazol, Propiconazol, Triflumizole, Prochloraz, Beflazoate, Fenarimol, Pyrifenox, Triforine, Flusilazole, Etaconazole, Dicloputrazole, Fluotrimazole, Flutriafen, Penconazole, Diniconazole, Imazalyl, Tridemorph, Fenpropimorph, Buthiobate, Epoxyconazole, Metoconazole, etc.

Antibiotics: Polyoxins, Blastocidin-S, Kasugamycin, Balidamycin, Dihydrostreptomycin sulfate, etc.

Others: Propamocarbhydrochloride, Quintozene, Hydroxyisoxazole, Metasulfocarb, Anilazine, Isoprothiolane, Probenazole, Quinomethionate, Dithianone, Dinocap, Diclomezine, Ferimzone, Fluazinam, Pyroquilon, Tricyclazole, Oxilinic acid, Dithianone, Iminoctadine acetate, Cymoxanil, Pyrrolenitrine, Metasulfocarb, Diethofencarb, Binapacryl, Lecithin, Sodium hydrogen atomcarbonate, Fenaminosulf, Dodine, Dimetomorph, Fenazine oxide, Carpropamide, Flusulfamide, Fludioxonil, Famoxidone, etc.

Insecticides and Acaricides

Organophosphorous and carbamate insecticides: Fenthion, Fenitrothion, Diazinon, Chlorpyrifos, ESP, Bamidothion, Fenthoate, Dimethoate, Formothion, Malathon, Trochlorfon, Thiometon, Phosmet, Dichlorvos, Acephate, EPBP, Methyl parathion, Oxadimeton methyl, Ethion, Salithion, Cyanophos, Isoxathione, Pyridafenthion, Phosalone, Methidathion, Sulprofos, Chlorfevinphos, Tetrachlorvinphos, Dimethylvinphos, Propaphos, Isofenphos, Ethyl thimeton, Profenophos, Pyraclofos, Monocrotophos, Azinphosmethyl, Aldicarb, Methomyl, Dithicarb, Carbofuran, Carbosulfan, Benflacarb, Flathiocarb, Propoxur, BPMC, MTMC, MIPC, carbaryl, Pyrimicarb, Rthifencarb, Fenoxycarb, etc.

Pyrethroid insecticides: Permethrin, Cypermethrin, Deltamethrin, Fenvalerate, Fenpropathrin, Pyrethrin, Allethrin, Tetramethrin, Resmethrin, Dimethrin, Propathrin, Fenothrin, Prothrin, Fluvarinate, Cyfluthrin, Cyhalothrin, Flucythrinate, Ethofenprox, Cycloprothrin, Tralimethrin, Silafluofen, Profenprox, Acrinathrin, etc.

Bezoyl urea and other insecticides: Diflubenzuron, Chlorfluazuron, Hexaflumuron, Triflumuron, Tetrabenzuron, Fulfenoxuron, Flucycloxuron, Buprofezin, Pyriproxyfen, Methoprene, Benzoepin, Diafenthiuron, Acetamiprid, Imidacloprid, Nitenpyram, Fipronyl, Cartap, Thiocyclam, Bensultap, Nicotin sulfate, Rotenone, Metaldehyde, Machine oil, Microbial insecticides such as BT and insect-pathogenic viruses, etc.

Nematicides: Fenamiphos, Fosthiazate, etc.

Acaricides

Chlorbenzilate, Fenisobromolate, Dicofol, Amitraz, BPPS, Benzomate, Hexythiazox, Fenbutatin oxide, Polynactin, Quinomethionate, CPCBS, Tetradifon, Avermectin, Milbemectin, Clofentezin, Cyhexatin, Pyridaben, Fehproxymate, Tebufenpyrad, Pyrimidifen, Fenothiocarb, Dienochlor, etc.

Plant Growth Regulators: Gibberellin s(e.g., Gibberellin A3, Gibberellin A$, Gibberellin A7), IAA, NAA, etc.

BEST MODES OF EMBODIMENTS FOR CARRYING OUT THE INVENTION

Now, the present invention will be described specifically by referring the Examples described below.

Example 1

Production of 1-(4,6-Dimethyl-2-pyridinyl)ethanone O-[(2-Fluoro-6-methoxyphenyl)methyl]oxime (Compound No. 1)

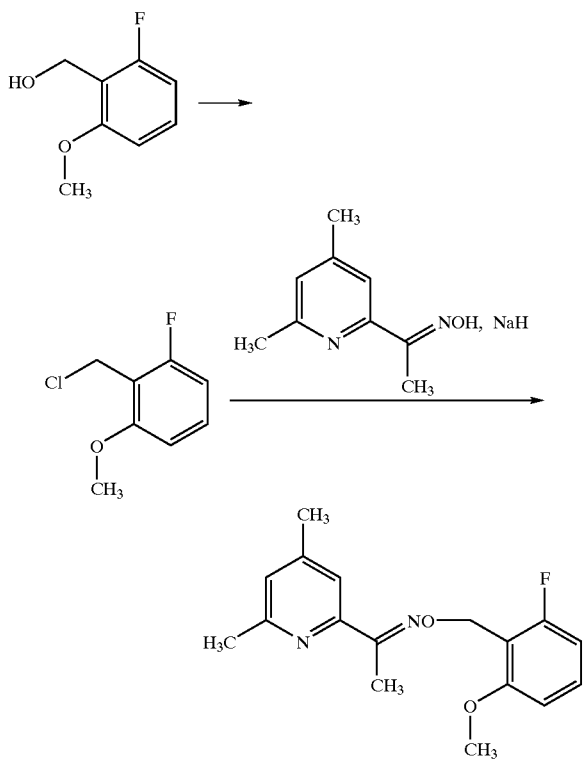

0.57 g (3.64 mmol) of 2-fluoro-6-methoxybenzyl alcohol was dissolved in 10 ml of benzene, and the resultant solution was added with 0.56 g (4.73 mmol) of thionyl chloride under a room temperature. The obtained solution was stirred for 1 hour at a room temperature to complete a reaction. The reacted solution was then condensed under reduced pressure to obtain a crude product of 2-fluoro-6-methoxybenzyl chloride.

On the other hand, 0.46 g (2.80 mmol) of 1-(4,6-dimethyl-2-pyridinyl)ethanone oxime was dissolved in 10 ml of N,N-dimethylformamide, and the resultant solution was added with 0.13 g (3.36 mmol) of sodium hydride (60%, oiliness) while cooling the solution with ice. Then, the obtained solution was stirred for 30 min. at the same temperature and subsequently added with the whole amount of the crude product of 2-fluoro-6-methoxybenzyl chloride obtained as described above while cooling the solution with ice. The resultant mixture was. further stirred for 40 min. at a room temperature, and the reacted mixture was poured into ice water and then subjected to an extraction with diethyl ether. The resultant nonaqueous layer was washed with water and the dried with anhydrous magnesium sulfate. The dried nonaqueous layer was then condensed under reduced pressure to obtain a crude product. Then, said crude product was purified by means of silica gel column chromatography (eluate; hexane:ethyl acetate=7:3 v/v) to obtain the target compound in an amount of 0.55 g. Melting point: 87–89° C.

Example 2

Production of 1-(4,6-Dimethyl-2-pyridinyl)ethanone O-[(2,4-Dimethoxyphenyl)methyl] Oxime (Compound No. 13)

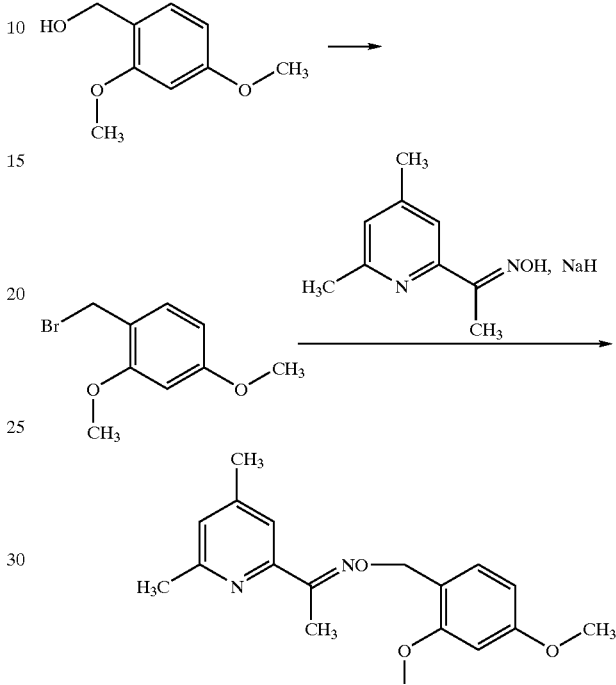

0.61 g (3.63 mmol) of 2,4-dimethoxybenzyl alcohol was dissolved in 9.2 ml of toluene, and the resultant solution was added with 0.3 ml of pyridine. The obtained transparent solution was cooled down to a temperature below 0° C. and subsequently fed dropwise with 1.8 ml toluene solution containing 0.98 g (3.62 mmol) of phosphorus tribromide in a manner of spending 20 min. The resultant solution was stirred for 35 min. to allow the compounds to react. The reacted solution was then poured into ice water, and the ice water was extracted with diethyl ether. The resultant nonaqueous layer was washed with water, saturated aqueous solution of sodium hydrogen atomcarbonate and sodium chloride solution, all of them were cooled in advance, in sequence, and then dried with anhydrous magnesium sulfate. The dried solution was then subjected to distillation under reduced pressure at approximately 30° C. using a rotary evaporator to distillate out diethyl ether contained in the solution, thereby obtaining a toluene solution of 2,4-dimethoxybenzyl chloride.

On the other hand, 0.50 g (3.05 mmol) of 1-(4,6-dimethyl-2-pyridinyl)ethanone oxime was dissolved in 5 ml of N,N-dimethylformamide, and the resultant solution was added with 0.12 g (3.00 mmol) of sodium hydride (60%, oiliness) while cooling the solution with ice. The obtained solution was stirred for 30 min. at a temperature below 0° C. and subsequently added with the whole amount of the toluene solution of 2,4-dimethoxybenzyl chloride prepared previously under cooling with ice. The resultant solution was stirred for 1.5 hours while cooling with ice, and the reacted solution was then poured into icewater, and the ice water containing the reacted solution was extracted with diethyl ether. The resultant nonaqueous layer was separated and washed with water and then dried with anhydrous magnesium sulfate. The dried layer was then condensed under reduced pressure to obtain a crude product. Then, said crude product was purified by means of silica gel column chromatography (eluate; hexane:ethyl acetate=7:3 (v/v)) to obtain the target compound in an amount of 0.62 g. $n_D^{20.7}$; 1.5722

Example 3

Production of 1-(4,6-Dimethyl-2-pyridinyl)ethanone O-[(2-Methoxy-6-methylphenyl)methyl] Oxime (Compound No. 7)

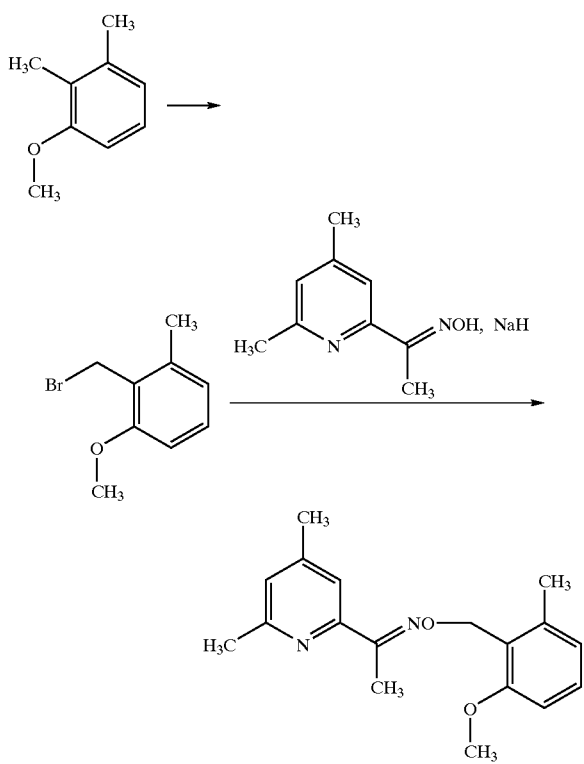

0.50 g (3.68 mmol) of 2,3-dimethylanisole was dissolve in 10 ml of carbon tetrachloride. The resultant solution was then added with 0.72 g (4.04 mmol) of N-bromosuccinimide, and the obtained solution was subjected to irradiation of light (Infrared lamp 375WR manufactured by Toshiba) for 45 min. at the reflux temperature. The solution was then cooled down, and the temperature thereof was maintained at a room temperature to cause the precipitation. The precipitated succinimide was separated by filtration, and the obtained filtrate was condensed under reduced pressure to produce a crude product of 2-methoxy-6-methylbenzyl bromide.

On the other hand, 0.50 g (3.05 mmol) of 1-(4,6-dimethyl-2-pyridinyl)ethanone oxime was dissolved in 10 ml of N,N-dimethylformamide, and the resultant solution was added with 0.12 g (3.00 mmol) of sodium hydride (60%, oiliness) under cooling with ice. The solution was then stirred for 30 min. at a temperature below 0° C. and then added with the whole amount of the crude product of 2-methoxy-6-methylbenzyl bromide prepared previously under cooling with ice. The resultant solution was stirred for an hour at a room temperature to complete a reaction, and the reacted solution was poured into ice water and subjected to an extraction with diethyl ether. The resultant nonaqueous layer was separated, and the separated layer was washed with water and then dried with anhydrous magnesium sulfate. The dried nonaqueous layer was then condensed under reduced pressure to produce a crude product. The crude product was then purified by means of silica gel column chromatography (eluate; hexane:ethyl acetate=7:3 (v/v)) and recrystallized in hexane to obtain the target compound in an amount of 0.30 g.

Melting point: 71–72° C.

Example 4

Production of 4,6-Dimethyl-2-pyridinecarboxyaldehyde O-[(2,6-Dimethoxyphenyl)methyl] Oxime (Compound No. 196)

i) Production of 4,6-dimethyl-2-pyridinecarboxyaldehyde

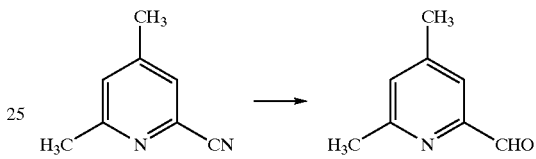

10.0 g (75.8 mmol) of 2-cyano-4,6-dimethylpyridine was dissolved in 100 ml of methylene chloride, and the resultant solution was cooled down, and the temperature thereof was maintained at −78° C. The solution was then fed dropwise in a manner of spending 20 min. with 87.8 ml (83.3 mmol) of 0.95M hydrogen atomated diisobutyl aluminium-toluene solution at the same temperature. The resultant solution was stirred for 1.8 hours at the same temperature and further stirred for 1.3 hours after elevating the temperature to a room temperature to complete a reaction. The reacted solution was then fed dropwise with 3N hydrochloric acid so as to discontinue the reaction, and then, the reacted solution was neutralized by an addition of 10% aqueous solution of sodium hydroxide for the following extraction step using chloroform. The obtained chloroform layer was dried with anhydrous magnesium sulfate and then condensed under reduced pressure to produce a crude reaction product. The obtained crude product was then purified by means of silica gel column chromatography (eluate; hexane:ethyl acetate= 9:1 (v/v)) to obtain the target compound in an amount of 0.34 g.

1H-NMR (CDCl$_3$, TMS, δ ppm) data: 2.40 (s, 3H), 2.61 (s, 3H), 7.20 (d, 1H), 7.60 (d, 1H), 10.02 (s, 1H).

ii) Production of 4,6-dimethyl-2-pyridinecarboxyaldoxime

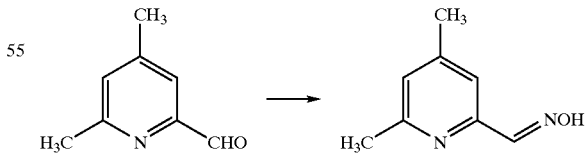

0.33 g (2.4 mmol) of 4,6-dimethyl-2-pyridinecarboxyaldehyde was dissolved in 5 ml of ethanol, and the resultant solution was added with 0.20 g (2.9 mmol) of hydroxylamine hydrochloride. The mixture was then heated to raise the temperature up to the reflux temperature and stirred for 35 min. After the stirring, the mixture was cooled down to a room temperature. The reacted solution obtained in acidic state was neutralized with 10% aqueous solution of sodium hydroxide. The solution was then extracted with ethyl acetate, and the resultant nonaqueous layer was separated, and then, dried with anhydrous magnesium sulfate, and condensed under reduced pressure to obtain the target compound in an amount of 0.32 g.

1H-NMR (CDCl₃, TMS, δ ppm) data: 2.33 (s, 3H), 2.57 (s, 3H), 6.99 (d,1H), 7.38 (d, 1H), 7.56 (br, 1H), 8.20 (s, 1H).

iv) Production of 4,6-dimethyl-2-pyridinecarboxyaldehyde O-[(2,6-dimethoxyphenyl)methyl] oxime

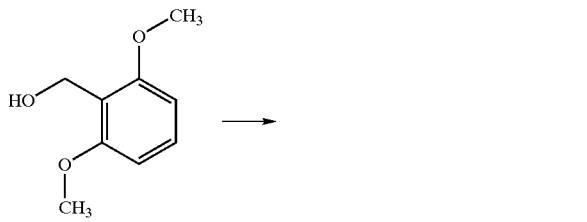

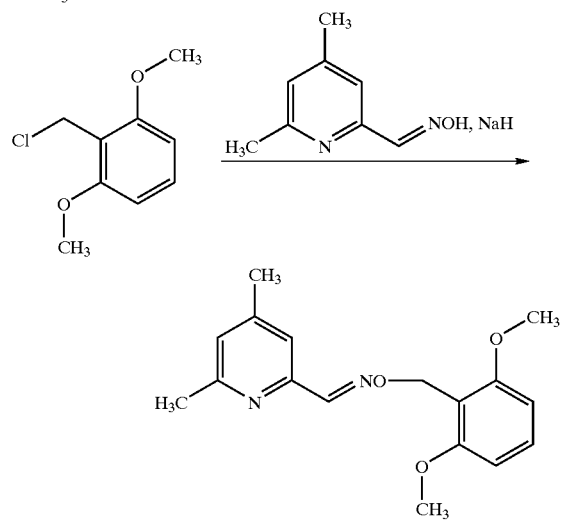

0.43 g (2.56 mmol) of 2,6-dimethoxybenzyl alcohol was dissolved in 5 ml of benzene, and the resultant solution was added with 0.40 g (3.36 mmol) of thionyl chloride at a room temperature. The mixture was then stirred for an hour at a room temperature to facilitate the provided compounds to react. The reacted solution was then condensed under reduced pressure to obtain a crude product of 2,6-dimethoxybenzyl chloride.

On the other hand, 0.32 g (2.13 mmol) of 4,6-dimethyl-2-pyridinecarboxyaldoxime was added into 5 ml of N,N-dimethylformamide to prepare a suspension thereof. The suspension was added with 0.11 g (2.75 mmol) of sodium hydride (60%, oiliness) while cooling the suspension with ice. The mixture was stirred for 25 min. at a temperature below 0° C., and then added with the whole amount of the crude product of 2,6-dimethoxybenzyl chloride prepared previously under cooling condition with ice. The mixture was stirred for two hours at a room temperature to facilitate the compounds in the mixture to react. The reacted mixture was poured into ice water, and the reacted mixture in the ice water was subjected to an extraction with diethyl ether. The resultant nonaqueous layer was separated, washed with water, and dried with anhydrous magnesium sulfate. The dried nonaqueous layer was then condensed under reduced pressure to obtain a crude product. The obtained crude product was purified by means of silica gel column chromatography (eluate; hexane:ethyl acetate=7:3 (v/v)) to obtain the target compound in an amount of 0.66 g. Melting point; 103–105° C.

Example 5

Production of 4-Chloro-6-methyl-2-pyridinecarboxyaldehyde O-[(2,6-Dimethoxyphenyl)methyl] Oxime (Compound No. 219)

i) Production of 4-chloro-6-methyl-2-pyridinylmethanol

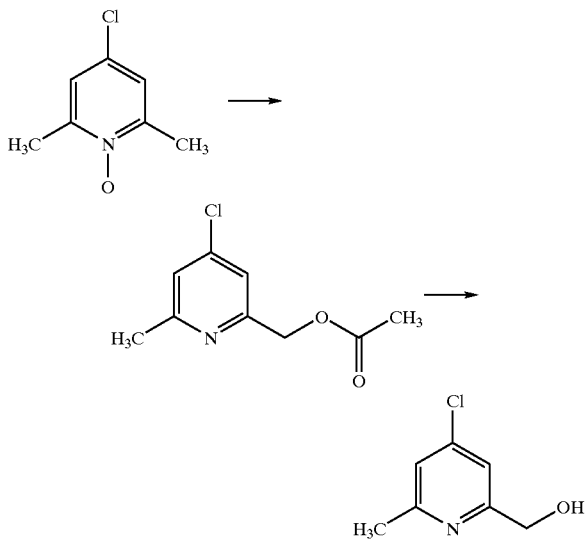

4.0 g (25.4 mmol) of 4-chloro-2,6-dimethylpyridine-1-oxide was dissolved in 12 ml of acetic anhydride. The resultant solution was gradually heated to raise the temperature to the reflux temperature, and the solution was then stirred overnight at the same temperature. The reacted solution was then condensed under reduced pressure to obtain a crude product of acetic 4-chloro-6-methyl-2-pyridinylmethyl ester.

The obtained crude product was dissolved in 14 ml of methanol, and the resultant solution was added with 7 ml of water and 0.9 g of potassium hydroxide. The obtained mixture was then stirred for 4 hours at a room temperature to react. The reacted solution was then condensed under reduced pressure to obtain a reaction product. The reaction product was then diluted with water, and the resultant solution was subjected to an extraction with ethyl acetate. The resultant nonaqueous layer was separated and washed with saturated saline solution and then dried with anhydrous magnesium sulfate. The dried nonaqueous layer was then condensed under reduced pressure to obtain a crude product. The obtained crude product was then purified by means of silica gel column chromatography (eluate; benzene:ethyl acetate=2:1 (v/v)) to obtain the target compound in an amount of 1.38 g.

ii) Production of 4-chloro-6-methyl-2-pyridinecarboxyaldehyde

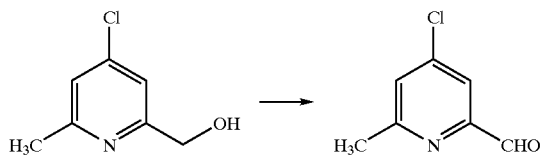

1.38 g (8.8 mmol) of 4-chloro-6-methyl-2-pyridinylmethanol was dissolved in 20 ml of benzene. The resultant solution was added with 3.3 g of activated manganese dioxide (manufactured by Aldrich), and the mixture was heated so as to elevate the temperature of the mixture to the reflux temperature. After the mixture has reached the reflux temperature, it was stirred continuously all night to complete a reaction. The reacted mixture was then cooled, and the temperature of the mixture was maintained at a room temperature. Then, the insoluble materials in the mixture were removed by filtration. The filtrate obtained was condensed under reduced pressure to obtain the target compound in an amount of 1.08 g.

1H-NMR (CDCl$_3$, TMS, δ ppm) data; 2.63 (s, 3H), 7.40 (d, 1H), 7.78 (d, 1H), 10.00 (s, 1H).

iii) Production of 4-chloro-6-methyl-2-pyridinecarboxyaldoxime

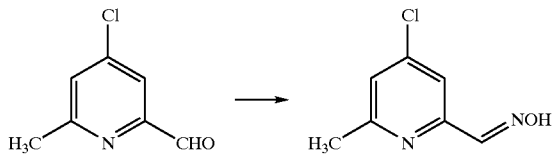

1.08 g (6.9 mmol) of 4-chloro-6-methyl-2-pyridinecarboxyaldehyde was dissolved in 15 ml of methanol. The resultant solution was added with 0.53 g (7.6 mmol) of hydroxylamine hydrochloride, and the obtained mixture was heated so as to maintain the temperature thereof at the reflux temperature. The mixture was then stirred for an hour at the same temperature to facilitate the compounds in the mixture to react, followed by cooling the reacted mixture down to a room temperature. The reacted solution obtained in acidic condition was then neutralized with an aqueous solution of sodium hydrogen atomcarbonate. The neutralized solution was then added with ethyl acetate to make an extraction therewith, and the resultant nonaqueous layer was dried with anhydrous magnesium sulfate and condensed under reduced pressure to thereby obtain the target compound. The yield amount in total of the target compound from the filtrate and the extract was found to be 1.13 g.

1H-NMR (CDCl$_3$, TMS, δ ppm) data; 2.57 (s, 3H), 7.16 (d, 1H), 7.61 (d, 1H), 8.15–8.28 (M, 2H).

iv) Production of 4-chlorro-6-methyl-2-pyridinecarboxyaldehyde O-[(2,6-dimethoxyphenyl)methyl] oxime

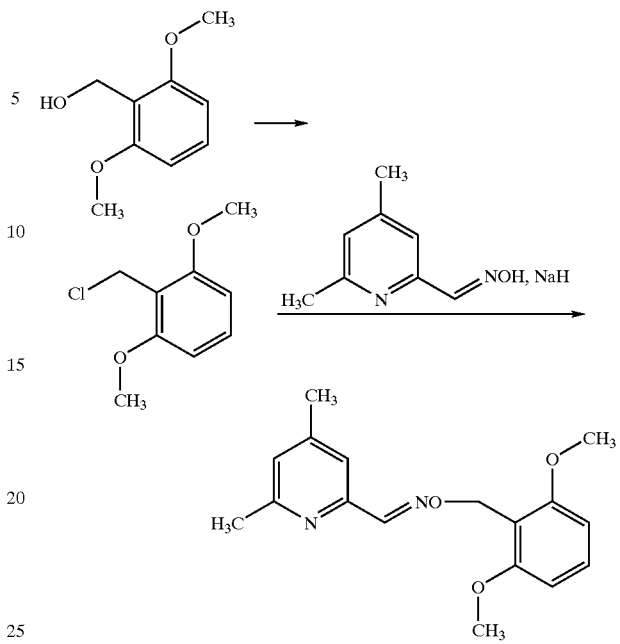

0.49 g (2.93 mmol) of 2,6-dimethoxybenzyl alcohol was dissolved in 6 ml of benzene, and the resultant solution was added with 0.41 g (3.32 mmol) of thionyl chloride at a room temperature. The thus obtained solution was then stirred for 1.5 hours at a room temperature to complete a reaction. The reacted solution was then condensed under reduced pressure to obtain a crude product of 2,6-dimethoxybenzyl chloride.

On the other hand, 0.50 g (2.93 mmol) of 4-chloro-6-methyl-2-pyridinecarboxyaldoxime was added into 5 ml of N,N-dimethylformamide to make a suspension, whereto 0.18 g (4.39 mmol) of sodium hydride (60%, oiliness) was added while cooling the suspension with ice. Then, the mixture was stirred for 30 min. at a temperature below 0° C., and added with the whole amount of the crude product of 2,6-dimethoxybenzyl chloride prepared previously while cooling the mixture with ice. The resultant mixture was then stirred for two hours at a room temperature to complete a reaction, and the reacted mixture was then poured into ice water. The ice water containing the mixture was extracted with diethyl ether, and the resultant nonaqueous layer was washed with water, dried with anhydrous magnesium sulfate, and condensed under reduced pressure to thereby obtain a crude product. The obtained crude product was then purified by means of silica gel column chromatography (eluate; hexane:ethyl acetate=7:3 (v/v)) to obtain the target compound in an amount of 0.66 g.

Melting point; 106–108° C.

Example 6

Production of 1-(4-Chloro-6-methyl-2-pyridinyl) ethanone O-[(2,6-Dimethoxyphenyl)methyl] Oxime (Compound No. 18)

i) Production of 4-chloro-2-cyano-6-methylpyridine

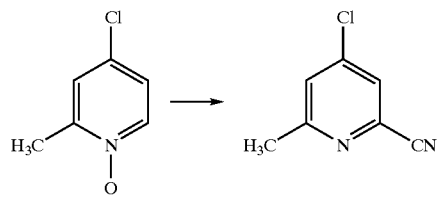

32 g (223 mmol) of 4-chloro-2-methylpyridine-1-oxide was dissolved in 250 ml of methylene chloride. The resultant solution was added with 24. 6 g (248 mmol) of trimethyl silylanilide at a room temperature in a manner of spending 5 min. The mixture was stirred for 10 min. and then added with 23. 5 g (219 mmol) of dimethylcarbamoyl chloride at the same temperature in a manner of spending 5 min. At that time, the inner temperature of the mixture had elevated to the reflux temperature thereof due to heat generated by the reaction. While stirring the mixture, the mixture was naturally cooled until the time that the inner temperature of the mixture falls to reach a room temperature. After stirring the mixture for 4 days, the reacted solution was cooled so as to maintain the temperature thereof at 5° C. and was added with 300 ml of 10% aqueous solution of sodium hydrogen atomcarbonate. The organic layer of the mixture was separated, and the aqueous layer was extracted with chloroform. The obtained chloroform layer was unified with the separated organic layer, and the unified mixture was dried with anhydrous magnesium sulfate and then condensed under reduced pressure to obtain a crude product. The obtained crude product was then purified by means of silica gel column chromatography (eluate; hexane:ethyl acetate= 4:1 (v/v)) to obtain the target compound in an amount of 10 g.

1H-NMR (CDCl₃, TMS, δ ppm) data; 2.60 (s, 3H), 7.40 (d, 1H), 7.53 (d, 1H).

ii) Production of 1-(4-chloro-6-methyl-2-pyridinyl)ethanone

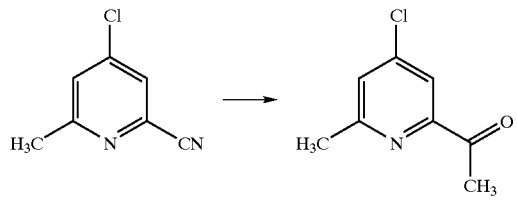

10 g (66 mmol) of 4-chloro-2-cyano-6-methylpyridine was dissolved in 100 ml of anhydrous diethyl ether. The resultant solution was cooled to maintain the temperature thereof at 5° C., and was then fed dropwise with 262 ml (87 mmol) of diethyl ether solution of 3M-methyl magnesium bromide (manufactured by Aldrich) at the same temperature in a manner of spending 15 min. At that time, the inner temperature of the mixture had elevated to 20° C. due to heat generated by the reaction. The mixture was stirred for 2.5 hours, then cooled down to 5° C. and added with aqueous solution of ammonium chloride to discontinue the reaction. The reacted mixture was extracted with diethyl ether, and the resultant nonaqueous layer was washed with water, then dried with anhydrous magnesium sulfate and condensed under reduced pressure to thereby obtain a crude product. The obtained crude product was purified by means of silica gel column chromatography (eluate; hexane:ethyl acetate= 4:1 (v/v)) to obtain the target compound in an amount of 3.8 g.

1H-NMR (CDCl₃, TMS, δ ppm) data; 2.61 (s, 3H), 2.70 (s, 3H), 7.32 (d, 1H), 7.83 (d, 1H).

iii) Production of 1-(4-chloro-6-methyl-2-pyridinyl) ethanone oxime

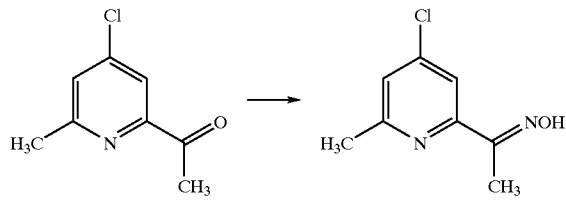

3.8 g (22.4 mmol) of 1-(4-chloro-6-methyl-2-pyridinyl) ethanone was dissolved in 40ml of methanol. The resultant solution was cooled to 5° C., and was added with 2.34 g (33.7 mmol) of hydroxylamine hydrochloride and 6.49 g (33.7 mmol) of 28% sodium methylate. The obtained mixture was then kept at a room temperature, then continuously stirred all night. The target compound will be precipitated in the mixture. The precipitation was then taken out by filtration, washed with hexane and dried to obtain the target compound in an amount of 3.3 g.

1H-NMR (CDCl₃, TMS, δ ppm) data; 2.35 (s, 3H), 2.57 (s, 3H), 7.13 (d, 1H), 7.63 (d, 1H), 8.1 (br, 1H).

iv) Production of 1-(4-chloro-6-methyl-2-pyridinyl) ethanone O-[(2,6-dimethoxyphenyl)methyl] oxime

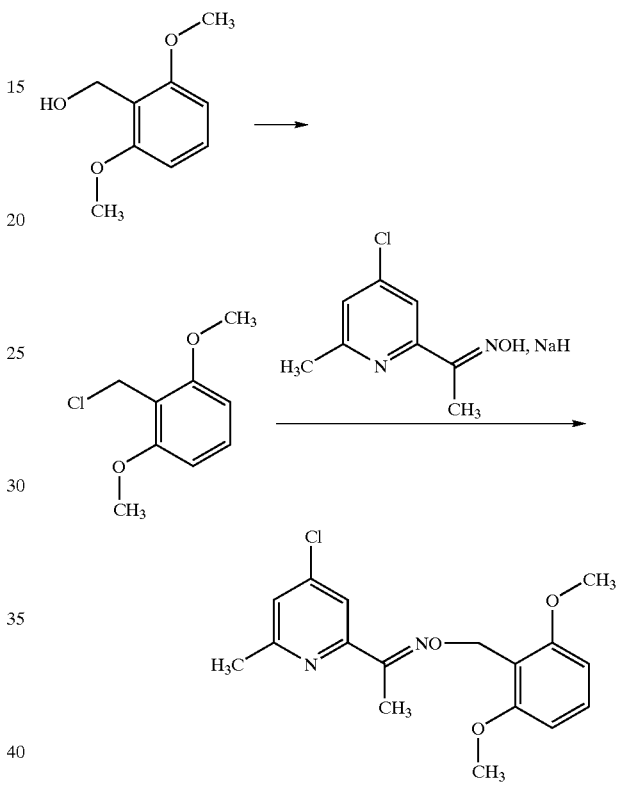

1.86 g (11.1 mmol) of 2,6-dimethoxybenzyl alcohol was dissolved in 15 ml of benzene, and the resultant solution was cooled to 5° C. The solution was then added with 1.55 g (13.0mmol) of thionyl chloride at the same temperature. The mixture was subjected to temperature elevation up to a room temperature, then stirred for 70 min. to complete a reaction. The reacted solution was condensed under reduced pressure to thereby obtain a crude product of 2,6-dimethoxybenzyl chloride.

On the other hand, 1.66 g (9.0 mmol) of 1-(4-chloro-6-methyl-2-pyridinyl)ethanone oxime was dissolved in 15 ml of N,N-dimethylformamide, and the resultant solution was added with 0.18 g (4.39 mmol) of sodium hydride (60%, oiliness) while cooling the solution with ice. The mixture was stirred for 15 min. at a temperature below 0° C. and was added with the whole amount of the crude product of 2,6-dimethoxybenzyl chloride prepared previously while cooling the mixture with ice. The resultant mixture was stirred for 2.3 hours at a room temperature to complete a reaction. The reacted mixture was then poured into ice water. At that time, the target compound was precipitated in the ice water. The precipitation was taken out by filtering, washed with hexane and dried to thereby obtain the target compound in an amount of 2.3 g.

Melting point; 105–106° C.

Example 7

Production of 4,6-Dimethyl-2-pyridinecarboxylaldehyde O-[(2-Methoxy-6-nitrophenyl)methyl] Oxime (Compound No. 217)

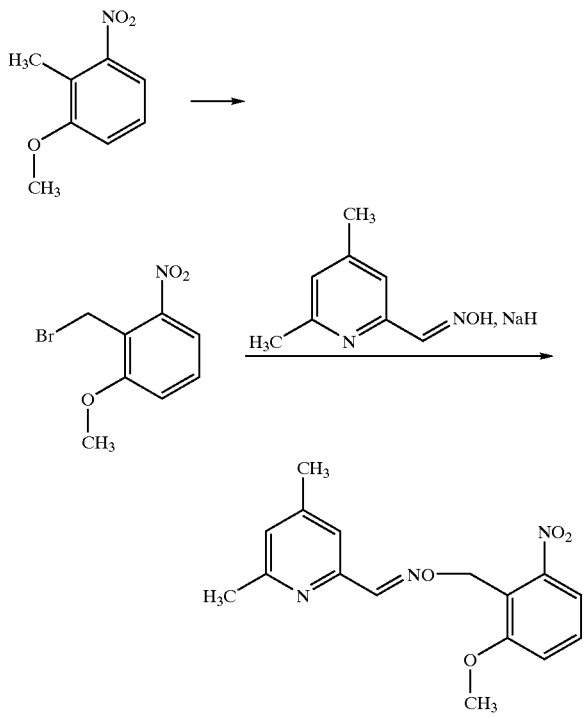

3.0 g (18 mmol) of 2-methyl-3-nitroanisole was dissolved in 500 ml of carbon tetrachloride. The resultant solution was added with 6.4 g (36 mmol) of N-bromosuccinimide, and the mixture was subjected to irradiation of light emitted from an infrared lamp of 375 W (manufactured by Toshiba) for 3 hours at the reflux temperature. The mixture was then cooled to a room temperature. Succinimide precipitated in the mixture was separated by filtration, and the obtained filtrate was condensed under reduced pressure to obtain a crude product of 2-methoxy-6-nitrobenzyl bromide.

On the other hand, 2.7 g (18 mmol) of 4,6-dimethyl-2-pyridinecarboxyaldoxime was added to 50 ml of N,N-dimethylformamide to prepare a suspension, and 0.86 g (21.6 mmol) of sodium hydride (60%, oiliness) was added into the suspension at a room temperature. The resultant mixture was then stirred for 30 min. at a room temperature, and was then added with the whole amount of the crude product of 2-methoxy-6-nitrobenzyl bromide prepared previously while cooling the mixture with ice. The mixture was then stirred for 3 hours at a room temperature to complete a reaction. The reacted mixture was poured into ice water, and the added ice water was extracted with diethyl ether. The resultant nonaqueous layer was washed with water, then dried with anhydrous magnesium sulfate and condensed under reduced pressure to thereby obtain a crude product. The obtained crude product was purified by means of silica gel column chromatography (eluate; benzene:ethyl acetate=20:1 (v/v)) to obtain the target compound in an amount of 3.1 g Melting point; 122–123° C.

Example 8

Production of 4,6-Dimethyl-2-pyridinecarboxyaldehyde O-[(2-Methoxy-6-aminophenyl)methyl] Oxime (Compound No. 222)

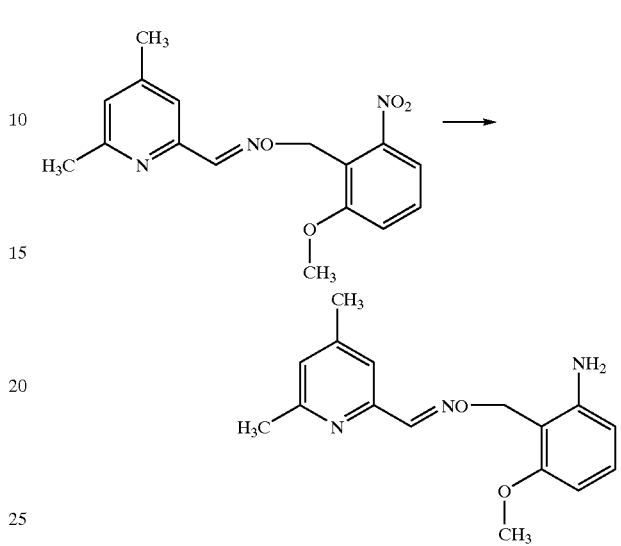

1.86 g (33.3 mmol) of electrolyzed iron powder (manufactured by Wako Pure Chemical), 20 ml of water and 1.2 g (20 mmol) of acetic acid were combined to prepare a suspension. The suspension was heated to reach 60° C., and was then fed dropwise with acetone solution (10 ml) containing 4,6-dimethyl-2-pyridinecarboxyaldehyde O-[(2-methoxy-6-bitrophenyl)methyl] oxime in an amount of 2.1 g (6.7 mmol) in a manner of spending 10 min. The resultant mixture was then stirred for 2 hours at the reflux temperature to complete a reaction. The reacted suspension was cooled to a room temperature and then diluted with ethyl acetate,. The reacted mixture was filtered with celite to eliminate insoluble materials. The resultant filtrate was extracted with ethyl acetate, and the obtained organic solvent layer was dried with anhydrous magnesium sulfate. The dried layer was then condensed under reduce pressure and subsequently purified by means of silica gel column chromatography (eluate; hexane:ethyl acetate=7:3 (v/v)) to obtain the target compound in an amount of 1.8 g Melting point; 115–117° C.

Example 9

Production of 4,6-Dimethyl-2-pyridinecarboxyaldehyde O-[(2-Methoxy-6-methylaminophenyl)methyl] Oxime (Compound No. 223)

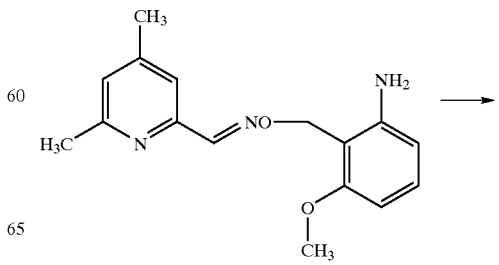

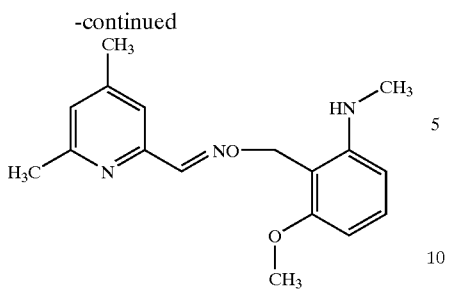

3.0 g (10.5 mmol) of 4,6-dimethyl-2-pyridinecarboxyaldehyde O-(2-methoxy-6-aminophenyl)methyl oxime was dissolved in 100 ml of acetonitrile. To the resultant solution was added 1.0 g (7.2 mmol) of potassium carbonate and 1.33 g (10.5 mmol) of dimethyl sulfate at a room temperature. The obtained mixture was stirred for 3 hours at the same temperature to complete a reaction. The reacted solution was then condensed under reduced pressure, added with water, and subsequently extracted with ethyl acetate. The resultant nonaqueous layer was dried with anhydrous magnesium sulfate and then condensed under reduced pressure to thereby obtain a crude product. The obtained crude product was then purified by means of silica gel column chromatography (eluate; hexane:ethyl acetate= 7:3 (v/v)) to obtain the target compound in an amount of 0.5 g.

Melting point; 115–117° C.

Furthermore, from the other fraction separated by the column chromatography, 0.3 g of 4,6-dimethyl-2-pyridinecarboxyaldehyde O-[(2-methoxy-6-dimethylaminophenyl)methyl] oxime (Compound No. 225) was obtained.

$n_D^{20.7}$ 1.5695

Example 10

Production of 1-(4,6-Dimethyl-2-pyridinyl)ethanone O-[(2-hydroxy-3-methoxyphenyl)methyl] Oxime (Compound No. 25)

i) Production of 1-(4,6-dimethyl-2-pyridinyl)ethanone O-[(2-methoxymethoxy-3-methoxyphenyl)methyl] oxime (Compound No. 255)

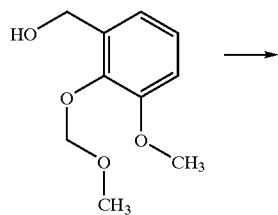

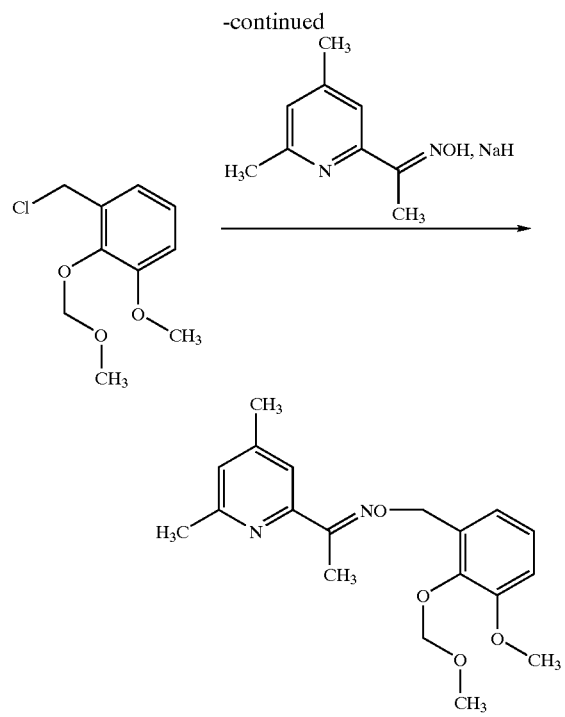

2.34 g (11.8 mmol) of 2-methoxymethoxy-3-methoxybenzyl alcohol was dissolved in 20 ml of diethyl ether, and the resultant solution was added with 1.53 g (11.8, mmol) of N,N-diisopropylethylamine. To the obtained solution was fed dropwise 1.40 g (11.8 mmol) of thionyl chloride and diethyl ether (15 ml) in a manner of spending 15 min. while cooling the solution with ice. The temperature of the resultant mixture was then brought back to a room temperature, and the mixture was stirred all night. The insoluble materials therein are removed by filtration, and the filtrate was condensed under reduced pressure to thereby obtain a crude product of 2-methoxymethoxy-3-methoxybenzyl chloride.

On the other hand, 1.94 g (11.8 mmol) of 1-(4,6-dimethyl-2-pyridinyl)ethanone oxime was dissolved in 20 ml of N,N-dimethylformamide, and the resultant solution was added with 0.71 g (17.7 mmol) of sodium hydride (60%, oiliness) while cooling the solution with ice. The obtained mixture was then stirred for 30 min. at a temperature below 0° C. and subsequently added with the whole amount of the crude product of 2-methoxymethoxy-3-methoxybenzyl chloride prepared previously while cooling the mixture with ice. The mixture was then stirred for 3 hours at a room temperature to complete a reaction. The reacted mixture was then poured into ice water, and subsequently subjected to an extraction with ethyl acetate. The resultant nonaqueous layer was washed with water, dried with anhydrous magnesium sulfate, and condensed under reduced pressure to thereby obtain a crude product. The obtained crude product was purified by means of silica gel column chromatography (eluate; hexane:ethyl acetate=4:1 (v/v)) to obtain the target compound in an amount of 1.77 g.

1H-NMR (CDCl$_3$, TMS, δ ppm) data: 2.31 (s, 3H), 2.36 (g, 3H), 2.51 (s, 3H), 3.62 (s, 3H), 3.86 (s, 3H), 5.16 (s, 2H), 5.40 (s, 2H), 6.86–7.13 (m, 4H), 7.51 (d, 1H).

ii) Production of 1-(4,6-dimethyl-2-pyridinyl)ethanone O-[(2-hydroxy-3-methoxyphenyl)methyl]oxime

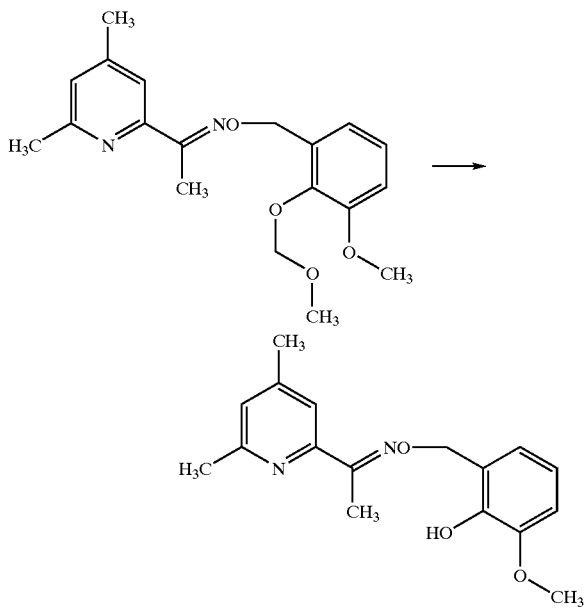

1.77 g (5.14 mmol) of 1-(4,6-dimethyl-2-pyridinyl) ethanone O-[(2-methoxymethoxy-3-methoxyphenyl) methyl] oxime was dissolved in 20 ml of tetrahydrofuran, and the resultant solution was added with 10 ml of 1N-hydrochloric acid. The obtained mixture was then heated to reach the reflux temperature and further stirred for an hour. Then, the mixture was cooled to a room temperature, neutralized with aqueous solution of 1N-sodium hydroxide and subjected to an extraction with diethyl ether. The resultant nonaqueous layer was washed with saturated saline solution, dried with anhydrous magnesium sulfate and then condensed under reduced pressure to thereby obtain the target compound in an amount of 1.6 g.

$n_D^{20.6}$ 1.5688

Example 11

Production of 1-(4,6-Dimethyl-2-pyridinyl)ethanone O-[(2-Pivaloyloxy-3-methoxyphenyl)methyl] Oxime (Compound No. 206)

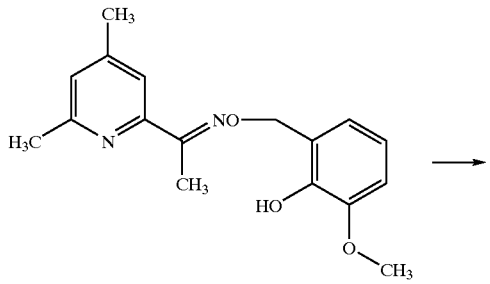

-continued

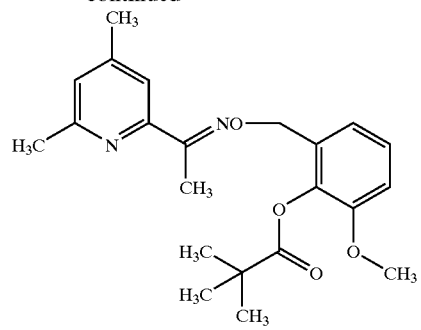

0.2 g (0.67 mmol) of 1-(4,6-dimethyl-2-pyridinyl) ethanone O-[(2-hydroxy-3-methoxyphenyl)methyl]oxime was dissolved in 5 ml of methylene chloride. The resultant solution was added with 0.11 g (1.34 mmol) of pyridine, 5 mg of 4-(N,N-dimethylamino)pyridine and 0.12 g (1.00 mmol) of pivalic chloride. The obtained mixture was heated to reach the reflux temperature and stirred for 5 hours to complete a reaction. The reacted solution was washed with water and saturated saline solution in sequence, and the resultant nonaqueous layer was dried with anhydrous magnesium sulfate. The mixture was then condensed under reduced pressure to obtain a crude product. The crude product was then purified by means of silica gel column chromatography (eluate; hexane:ethyl acetate=9:1 (v/v)) to obtain the target compound in an amount of 0.2 g.

1H-NMR (CDCl$_3$, TMS, δ ppm) data: 1.39 (s, 9H), 2.30 (s, 3H), 2.32 (s, 3H), 2.50 (s, 3H), 3.80 (s, 3H), 5.29 (s, 2H), 6.88–7.23 (m, 4H9, 7.48 (d, 1H).

Example 12

Production of 4,6-Dimethyl-2-pyridinecarboxyaldehyde O-[(2-Methoxy-6-bromophenyl)methyl]oxime (Compound No. 234)

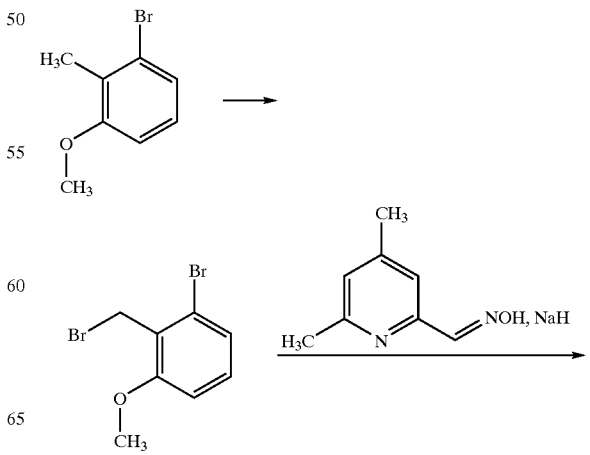

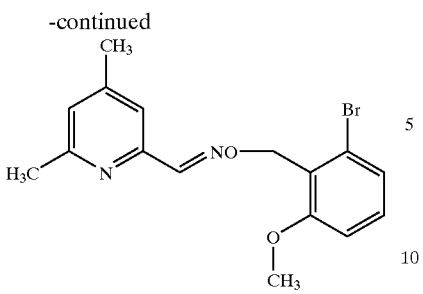

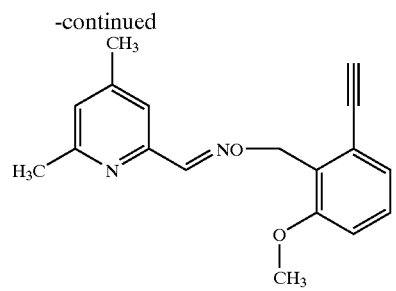

2.37 g (11.8 mmol) of 2-methyl-3-bromoanisole was dissolved in 100 ml of carbon tetrachloride. The resultant solution was added with 2.3 g (13.0 mmol) of N-bromosuccinimide, and the obtained mixture was subjected to irradiation of light emitted from an infrared lamp of 375 W (manufactured by Toshiba) for an hour at the reflux temperature. Then, the mixture was cooled to a room temperature. A precipitation generated in the mixture was separated by filtration, and the obtained filtrate was condensed under reduced pressure to obtain a crude product consisting of 2-methoxy-6-bromobenzyl bromide.

On the other hand, 1.77 g (11.8 mmol) of 4,6-dimethyl-2-pyridinecarboxyaldoxime was added to 20 ml of N,N-dimethylformamide to prepare a suspension thereof, and 0.52 g (13.0 mmol) of sodium hydride (60% oiliness) was added to the suspension at a room temperature. The resultant mixture was stirred for 30 min. at a room temperature and then added with the whole amount of the crude product of 2-methoxy-6-bromobenzyl bromide prepared previously at the same temperature. The obtained mixture was further stirred for 2 hours to complete a reaction, and the reacted solution was poured into ice water. The mixture in the ice water was the extracted with diethyl ether, and the resultant nonaqueous layer was washed with water, dried with anhydrous magnesium sulfate and then condensed under reduced pressure to thereby obtain a crude product. The obtained crude product was purified by means of silica gel column chromatography (eluate; benzene:ethyl acetate=20:1 (v/v)) to obtain the target compound in an amount of 3.67 g.

Melting point; 68–70° C.

Example 13

Production of 4,6-Dimethyl-2-pyridinecarboxyaldehyde O-[(2-Methoxy-6-ethynylphenyl)methyl]oxime (Compound No. 235)

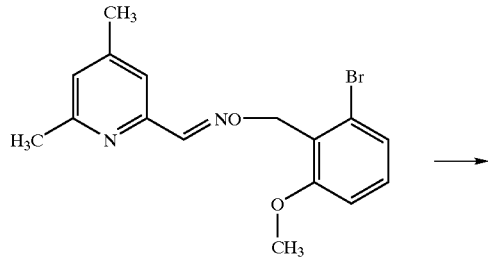

1.00 g (2.86 mmol) of 4,6-dimethyl-2-pyridinecarboxyaldehyde O-[(2-methoxy-6-bromophenyl)methyl]oxime was dissolved in 20 ml of triethylamine. The resultant solution was added with 0.56 g (5.72 mmol) of trimethylsilyl acetylene, 0.2 g (0.29 mmol) of bis-triphenylphosphine palladium(II) chloride, and 0.1 g (0.57 mmol) of copper(I) iodide in sequence. The obtained mixture was heated to reach the reflux temperature, where it was stirred for 2 hours to complete a reaction. The reacted solution was condensed under reduced pressure to obtain the reacted product. By means of let the reacted product to pass through a short-pass column chromatography, a crude product of 4,6-dimethyl-2-pyridinecarboxyaldehyde O-[(2-methoxy-6-trimethylsilylethynylphenyl)methyl] oxime in an amount of 0.81 g was obtained. The crude product was then dissolved in 10 ml of ethanol and further added with 0.31 g of potassium carbonate at a room temperature. The mixture was then stirred for an hour at the same temperature to complete a reaction. The reacted mixture was condensed under reduced pressure, added with water, and then extracted with diethyl ether. The resultant nonaqueous layer was washed with water, dried with anhydrous magnesium sulfate, and condensed under reduced pressure to thereby obtain a crude product. The obtained crude product was purified by means of silica gel column chromatography (eluate; benzene:ethyl acetate=20:1 (v/v)) to obtain the target compound in an amount of 0.15 g.

Melting point; 116–118° C.

Example 14

Production of 4,6-Dimethyl-2-pyridinecarboxyaldehyde O-[(2,4,6-Trimethoxyphenyl)methyl]oxime (Compound No. 233)

i) Production of N-(2,4,6-trimethoxybenzyloxy)phthalimide

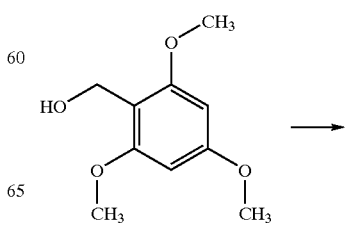

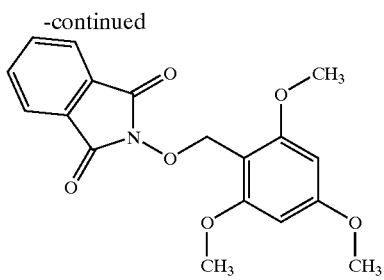

1.1 g (6.74 mmol) of N-hydroxyphthalimide was dissolved in 20 ml of dried tetrahydrofuran. The resultant solution was added with 2.65 g (10.1 mmol) of triphenylphosphine, 2.0 g (10.1 mmol) of 2,4,6-trimethoxybenzyl alcohol and 10 ml tetrahydrofuran solution containing 1.76 g (10.1 mmol) of diethyl azodicarboxylate in sequence at a room temperature. The obtained mixture was stirred for an hour at a room temperature and then added with water for the subsequent extraction with ethyl acetate. The resultant nonaqueous layer was dried with anhydrous magnesium sulfate and then condensed under reduced pressure to produce a precipitation. The obtained precipitation was taken out by filtration and the washed with diethyl ether to thereby obtain the target compound in an amount of 1.5 g.

ii) Production of 2,4,6-trimethoxybenzyloxyamine

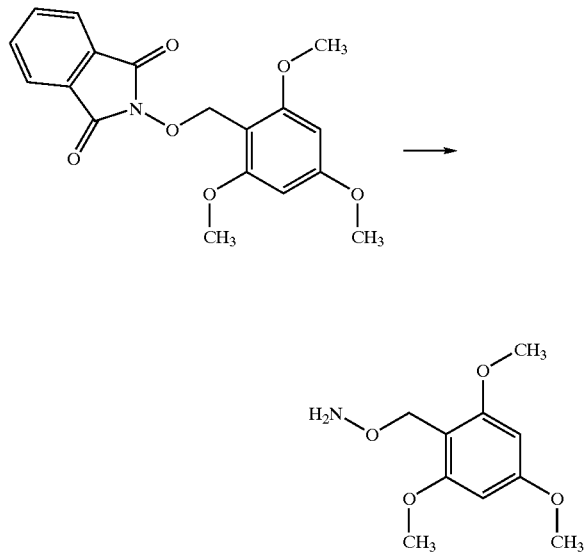

1.5 g (4.37 mmol) of N-(2,4,6-trimethoxybenzyloxy)phthalimide was dissolved in 50 ml of methanol. The resultant solution was added with 0.24 g (4.81 mmol) of hydrazine hydrate at a room temperature. The obtained mixture was stirred for an hour at the same temperature to complete a reaction. The mixture was then condensed under reduced pressure, and was subsequently added with water and ethyl acetate in sequence to cause impurities to precipitate. After the precipitated impurities are removed by a filtration, the mixture was extracted with ethyl acetate. The resultant nonaqueous layer was washed with water, dried with anhydrous magnesium sulfate and condensed under reduced pressure to thereby obtain the target compound in an amount of 0.85 g.

iii) Production of 4,6-dimethyl-2-pyridinecarboxyaldehyde O-[(2,4,6-trimethoxyphenyl)methyl]oxime

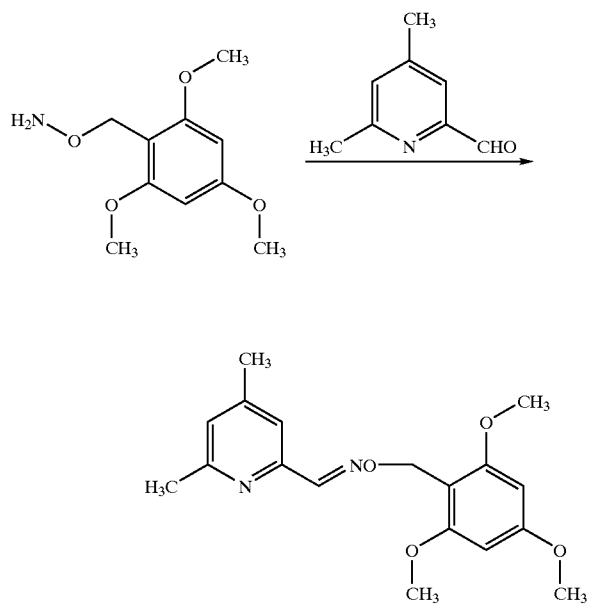

0.49 g (3.62 mmol) of 4,6-dimethyl-2-pyridinecarboxyaldehyde was dissolved in 10 ml of acetic acid, and the resultant solution was added with 10 ml acetic acid solution containing sodium acetate in an amount of 0.3 g (3.62 mmol) at a room temperature. The mixture was further added with 0.85 g (4.02 mmol) of 2,4,6-trimethoxybenzyloxyamine at the same temperature and then stirred for an hour to complete a reaction. The reacted mixture was condensed under reduced pressure, added with water and then extracted with ethyl acetate. The resultant nonaqueous layer was washed with an aqueous solution of sodium hydrogen atomcarbonate and then dried with anhydrous magnesium sulfate. The dried layer was condensed under reduced pressure to obtain a crude product. The crude product was then purified by means of silica gel column chromatography (eluate; hexane:ethyl acetate=7:3 (v/v)) to obtain the target compound in an amount of 0.05 g.

Melting point; 125–127° C.

The representative examples of the compounds according to the present invention as well as the compounds described in the Examples are presented in Table 1.

Incidentally, in the Table 1, the compounds for which the mark * is given in the column of "Physical Constant" are ones which have their NMR data in the bottom of the Table 1, respectively.

The abbreviations in Table 1 denote as follows. Me: methyl, Et: ethyl, Pr: propyl, Bu: butyl, Ph: phenyl, n: normal, i: iso, and t: tertiary,

TABLE 1

| No. | R¹ | R² | R³ | R⁴ | R⁵ | R⁶ | Physical Constant |
|---|---|---|---|---|---|---|---|
| 1 | 4,6-Me$_2$ | Me | H | H | Me | 6-F | mp 87–89° C. |
| 2 | 4,6-Me$_2$ | Me | H | H | Me | 3-Br-6-OMe | mp 69–71° C. |
| 3 | 4,6-Me$_2$ | Me | H | H | Me | 3-Cl-6-OMe | mp 60–62° C. |
| 4 | 4,6-Me$_2$ | Me | Me | H | Me | 3-Br-6-OMe | $n_D^{19.1}$ 1.5621 |
| 5 | 4-OMe-6-Me | Me | H | H | Me | 6-OMe | mp 114–115.5° C. |
| 6 | 4,6-Me$_2$ | Me | H | H | CH$_2$OMe | 4-OMe | $n_D^{18.1}$ 1.5594 |
| 7 | 4,6-Me$_2$ | Me | H | H | Me | 6-Me | mp 71–72° C. |
| 8 | 4,6-Me$_2$ | Me | H | H | Me | 3,6-(OMe)$_2$ | mp 76–78° C. |
| 9 | 4,6-Me$_2$ | Me | H | H | Me | 3-Br-5-Cl-6-OMe | mp 127–129° C. |
| 10 | 4-SMe-6-Me | Me | H | H | Me | 6-OMe | mp 153–154.5° C. |
| 11 | 4,6-Me$_2$ | Me | Me | H | Me | 6-OMe | mp 77–78° C. |
| 12 | 4,6-Me$_2$ | Me | H | H | CH$_2$OMe | 5-OMe | $n_D^{21.5}$ 1.5524 |
| 13 | 4,6-Me$_2$ | Me | H | H | Me | 4-OMe | $n_D^{20.7}$ 1.5722 |
| 14 | 4,6-Me$_2$ | Me | H | H | H | 4-OMe | $n_D^{18.1}$ 1.5671 |
| 15 | 4,6-Me$_2$ | Me | H | H | Me | 4-Me | $n_D^{17.4}$ 1.5540 |
| 16 | 4,6-Me$_2$ | Me | H | H | Me | 3,5-Cl$_2$-6-OMe | mp 128–130° C. |
| 17 | 4,6-Me$_2$ | Me | H | H | Me | 3-Br-5,6-(OMe)$_2$ | $n_D^{19.4}$ 1.5716 |
| 18 | 4-Cl-6-Me | Me | H | H | Me | 6-OMe | mp 105–106° C. |
| 19 | 4-(NMe$_2$)-6-Me | Me | H | H | Me | 6-OMe | mp 125–126° C. |
| 20 | 4,6-Me$_2$ | Et | H | H | Me | 6-OMe | mp 89–90° C. |
| 21 | 4,6-Me$_2$ | Me | H | H | H | 5-OMe | $n_D^{19.8}$ 1.5765 |
| 22 | 4,6-Me$_2$ | Me | H | H | Me | 5-OMe | $n_D^{21.0}$ 1.5451 |
| 23 | 4,6-Me$_2$ | Me | H | H | CH$_2$OMe | 6-OMe | mp 68–69° C. |
| 24 | 4,6-Me$_2$ | Me | H | H | H | 6-OMe | mp 110–111° C. |
| 25 | 4,6-Me$_2$ | Me | H | H | H | 3-OMe | $n_D^{20.6}$ 1.5688 |
| 26 | 4,6-Me$_2$ | Me | H | H | Me | 5-Me | $n_D^{15.9}$ 1.5608 |
| 27 | 4,6-Me$_2$ | Me | H | H | Me | 6-Et | mp 65–66° C. |
| 28 | 4,6-Me$_2$ | Me | H | H | Me | 6-OEt | |
| 29 | 4,6-Me$_2$ | Me | H | H | Me | 6-Cl | mp 79–80° C. |
| 30 | 4,6-Me$_2$ | Me | H | H | Me | 6-CF$_3$ | mp 94–95° C. |
| 31 | 4-Cl-6-Me | Me | H | H | Me | 6-Me | mp 96–97° C. |
| 32 | 4-F-6-Me | Me | H | H | Me | 6-Me | |
| 33 | 4-CF$_3$-6-Me | Me | H | H | Me | 6-Me | |
| 33 | 4-F-6-Me | Me | H | H | Me | 6-OMe | |
| 34 | 4-CF$_3$-6-Me | Me | H | H | Me | 6-OMe | mp 114–116° C. |
| 35 | 4-Me | Me | H | H | Me | 6-OMe | |
| 36 | 4-Me | Me | H | H | Me | 6-Me | $n_D^{23.5}$ 1.5771 |
| 37 | 4,6-Me$_2$ | Me | H | H | H | 3-Me | mp 76–78° C. |
| 38 | 4,6-Me$_2$ | Me | H | H | H | 3-Cl | |
| 39 | 4-Cl-6-Me | Me | H | H | H | 3-OMe | |
| 40 | 4-Cl-6-Me | Me | H | H | H | 3-Me | |
| 41 | 4-Cl-6-Me | Me | H | H | H | 3-Cl | |
| 42 | 4-F-6-Me | Me | H | H | H | 3-OMe | |
| 43 | 4-F-6-Me | Me | H | H | H | 3-Me | |
| 44 | 4-F-6-Me | Me | H | H | H | 3-Cl | |
| 45 | 4-CF$_3$-6-Me | Me | H | H | H | 3-OMe | |
| 46 | 4-CF$_3$-6-Me | Me | H | H | H | 3-Me | |
| 47 | 4-CF$_3$-6-Me | Me | H | H | H | 3-Cl | |
| 48 | 4,6-Me$_2$ | H | H | H | Me | 3-F-6-OMe | mp 50–51° C. |
| 49 | 4,6-Me$_2$ | Me | H | H | H | 4-Me | mp 98–99° C. |
| 50 | 4,6-Me$_2$ | Me | H | H | H | 4-Cl | |
| 51 | 4-Cl-6-Me | Me | H | H | H | 4-OMe | |
| 52 | 4-Cl-6-Me | Me | H | H | H | 4-Me | |
| 53 | 4-Cl-6-Me | Me | H | H | H | 4-Cl | |
| 54 | 4-F-6-Me | Me | H | H | H | 4-OMe | |
| 55 | 4-F-6-Me | Me | H | H | H | 4-Me | |
| 56 | 4-F-6-Me | Me | H | H | H | 4-Cl | |
| 57 | 4-CF$_3$-6-Me | Me | H | H | H | 4-OMe | |
| 58 | 4-CF$_3$-6-Me | Me | H | H | H | 4-Me | |
| 59 | 4-CF$_3$-6-Me | Me | H | H | H | 4-Cl | |
| 60 | 4,6-Me$_2$ | Me | H | H | H | 3-OMe-6-Me | |
| 61 | 4,6-Me$_2$ | Me | H | H | H | 3,6-Me$_2$ | |
| 62 | 4,6-Me$_2$ | Me | H | H | H | 3-Cl-6-Me | |
| 63 | 4-Cl-6-Me | Me | H | H | H | 3-OMe-6-Me | |
| 64 | 4-Cl-6-Me | Me | H | H | H | 3,6-Me$_2$ | |
| 65 | 4-Cl-6-Me | Me | H | H | H | 3-Cl-6-Me | |
| 66 | 4-F-6-Me | Me | H | H | H | 3-OMe-6-Me | |

TABLE 1-continued

| | | | | | | | |
|---|---|---|---|---|---|---|---|
| 67 | 4-F-6-Me | Me | H | H | H | 3,6-Me$_2$ | |
| 68 | 4-F-6-Me | Me | H | H | H | 3-Cl-6-Me | |
| 69 | 4-CF$_3$-6-Me | Me | H | H | H | 3-OMe-6-Me | |
| 70 | 4-CF$_3$-6-Me | Me | H | H | H | 3,6-Me$_2$ | |
| 71 | 4-CF$_3$-6-Me | Me | H | H | H | 3-Cl-6-Me | |
| 72 | 4,6-Me$_2$ | Me | H | H | H | 3,6-(OMe)$_2$ | mp 140–141° C. |
| 73 | 4,6-Me$_2$ | Me | H | H | H | 6-OMe-3-Me | |
| 74 | 4,6-Me$_2$ | Me | H | H | H | 6-OMe-3-Cl | |
| 75 | 4-Cl-6-Me | Me | H | H | H | 3,6-(OMe)$_2$ | |
| 76 | 4-Cl-6-Me | Me | H | H | H | 6-OMe-3-Me | |
| 77 | 4-Cl-6-Me | Me | H | H | H | 6-OMe-3-Cl | |
| 78 | 4-F-6-Me | Me | H | H | H | 3,6-(OMe)$_2$ | |
| 79 | 4-F-6-Me | Me | H | H | H | 6-OMe-3-Me | |
| 80 | 4-F-6-Me | Me | H | H | H | 6-OMe-3-Cl | |
| 81 | 4-CF$_3$-6-Me | Me | H | H | H | 3,6-(OMe)$_2$ | |
| 82 | 4-CF$_3$-6-Me | Me | H | H | H | 6-OMe-3-Me | |
| 83 | 4-CF$_3$-6-Me | Me | H | H | H | 6-OMe-3-Cl | |
| 84 | 4,6-Me$_2$ | Me | H | H | H | 6-Cl-3-OMe | |
| 85 | 4,6-Me$_2$ | Me | H | H | H | 6-Cl-3-Me | |
| 86 | 4,6-Me$_2$ | Me | H | H | H | 3,6-Cl$_2$ | |
| 87 | 4-Cl-6-Me | Me | H | H | H | 6-Cl-3-OMe | |
| 88 | 4-Cl-6-Me | Me | H | H | H | 6-Cl-3-Me | |
| 89 | 4-Cl-6-Me | Me | H | H | H | 3,6-Cl$_2$ | |
| 90 | 4-F-6-Me | Me | H | H | H | 6-Cl-3-OMe | |
| 91 | 4-F-6-Me | Me | H | H | H | 6-Cl-3-Me | |
| 92 | 4-F-6-Me | Me | H | H | H | 3,6-Cl$_2$ | |
| 93 | 4-CF$_3$-6-Me | Me | H | H | H | 6-Cl-3-OMe | |
| 94 | 4-CF$_3$-6-Me | Me | H | H | H | 6-Cl-3-Me | |
| 95 | 4-CF$_3$-6-Me | Me | H | H | H | 3,6-Cl$_2$ | |
| 96 | 4,6-Me$_2$ | Me | H | H | H | 4-OMe-6-Me | |
| 97 | 4,6-Me$_2$ | Me | H | H | H | 4,6-Me$_2$ | |
| 98 | 4,6-Me$_2$ | Me | H | H | H | 4-Cl-6-Me | |
| 99 | 4-Cl-6-Me | Me | H | H | H | 4-OMe-6-Me | |
| 100 | 4-Cl-6-Me | Me | H | H | H | 4,6-Me$_2$ | |
| 101 | 4-Cl-6-Me | Me | H | H | H | 4-Cl-6-Me | |
| 102 | 4-F-6-Me | Me | H | H | H | 4-OMe-6-Me | |
| 103 | 4-F-6-Me | Me | H | H | H | 4,6-Me$_2$ | |
| 104 | 4-F-6-Me | Me | H | H | H | 4-Cl-6-Me | |
| 105 | 4-CF$_3$-6-Me | Me | H | H | H | 4-OMe-6-Me | |
| 106 | 4-CF$_3$-6-Me | Me | H | H | H | 4,6-Me$_2$ | |
| 107 | 4-CF$_3$-6-Me | Me | H | H | H | 4-Cl-6-Me | |
| 108 | 4,6-Me$_2$ | Me | H | H | H | 4,6-(OMe)$_2$ | |
| 109 | 4,6-Me$_2$ | Me | H | H | H | 6-OMe-4-Me | |
| 110 | 4,6-Me$_2$ | Me | H | H | H | 6-OMe-4-Cl | |
| 111 | 4-Cl-6-Me | Me | H | H | H | 4,6-(OMe)$_2$ | |
| 112 | 4-Cl-6-Me | Me | H | H | H | 6-OMe-4-Me | |
| 113 | 4-Cl-6-Me | Me | H | H | H | 6-OMe-4-Cl | |
| 114 | 4-F-6-Me | Me | H | H | H | 4,6-(OMe)$_2$ | |
| 115 | 4-F-6-Me | Me | H | H | H | 6-OMe-4-Me | |
| 116 | 4-F-6-Me | Me | H | H | H | 6-OMe-4-Cl | |
| 117 | 4-CF$_3$-6-Me | Me | H | H | H | 4,6-(OMe)$_2$ | |
| 118 | 4-CF$_3$-6-Me | Me | H | H | H | 6-OMe-4-Me | |
| 119 | 4-CF$_3$-6-Me | Me | H | H | H | 6-OMe-4-Cl | |
| 120 | 4,6-Me$_2$ | Me | H | H | H | 6-Cl-4-OMe | |
| 121 | 4,6-Me$_2$ | Me | H | H | H | 6-Cl-4-Me | |
| 122 | 4,6-Me$_2$ | Me | H | H | H | 4,6-Cl$_2$ | |
| 123 | 4-Cl-6-Me | Me | H | H | H | 6-Cl-4-OMe | |
| 124 | 4-Cl-6-Me | Me | H | H | H | 6-Cl-4-Me | |
| 125 | 4-Cl-6-Me | Me | H | H | H | 4,6-Cl$_2$ | |
| 126 | 4-F-6-Me | Me | H | H | H | 6-Cl-4-OMe | |
| 127 | 4-F-6-Me | Me | H | H | H | 6-Cl-4-Me | |
| 128 | 4-F-6-Me | Me | H | H | H | 4,6-Cl$_2$ | |
| 129 | 4-CF$_3$-6-Me | Me | H | H | H | 6-Cl-4-OMe | |
| 130 | 4-CF$_3$-6-Me | Me | H | H | H | 6-Cl-4-Me | |
| 131 | 4-CF$_3$-6-Me | Me | H | H | H | 4,6-Cl$_2$ | |
| 132 | 4,6-Me$_2$ | Me | H | H | CH$_2$OMe | 3-OMe-6-Me | |
| 133 | 4-Cl-6-Me | Me | H | H | CH$_2$OMe | 3-OMe-6-Me | |
| 134 | 4-CF$_3$-6-Me | Me | H | H | CH$_2$OMe | 3-OMe-6-Me | |
| 135 | 4,6-Me$_2$ | Me | H | H | CH$_2$OCH$_2$Ph | 3-OMe-6-Me | |
| 136 | 4-Cl-6-Me | Me | H | H | CH$_2$OCH$_2$Ph | 3-OMe-6-Me | |
| 137 | 4-CF$_3$-6-Me | Me | H | H | CH$_2$OCH$_2$Ph | 3-OMe-6-Me | |
| 138 | 4,6-Me$_2$ | Me | H | H | CH$_2$O(CH$_2$)$_2$OMe | 3-OMe-6-Me | |
| 139 | 4-Cl-6-Me | Me | H | H | CH$_2$O(CH$_2$)$_2$OMe | 3-OMe-6-Me | |
| 140 | 4-CF$_3$-6-Me | Me | H | H | CH$_2$O(CH$_2$)$_2$OMe | 3-OMe-6-Me | |
| 141 | 4,6-Me$_2$ | Me | H | H | CH$_2$Ph | 3-OMe-6-Me | |
| 142 | 4-Cl-6-Me | Me | H | H | CH$_2$Ph | 3-OMe-6-Me | |
| 143 | 4-CF$_3$-6-Me | Me | H | H | CH$_2$Ph | 3-OMe-6-Me | |
| 144 | 4,6-Me$_2$ | Me | H | H | C(O)Me | 3-OMe-6-Me | |
| 145 | 4-Cl-6-Me | Me | H | H | C(O)Me | 3-OMe-6-Me | |

TABLE 1-continued

| | | | | | | | |
|---|---|---|---|---|---|---|---|
| 146 | 4-CF$_3$-6-Me | Me | H | H | C(O)Me | 3-OMe-6-Me | |
| 147 | 4,6-Me$_2$ | Me | H | H | C(C)Pr$^n$ | 3-OMe-6-Me | |
| 148 | 4-Cl-6-Me | Me | H | H | C(O)Pr$^n$ | 3-OMe-6-Me | |
| 149 | 4-CF$_3$-6-Me | Me | H | H | C(O)Pr$^n$ | 3-OMe-6-Me | |
| 150 | 4-Cl | Me | H | H | Me | 6-OMe | |
| 151 | 4-Cl | Me | H | H | Me | 6-Me | |
| 152 | 4-Cl | Me | H | H | H | 3-OMe | |
| 153 | 4-Cl | Me | H | H | H | 3-OMe-6-Me | |
| 154 | 4,5-Me$_2$ | Me | H | H | Me | 6-OMe | mp 132–133° C. |
| 155 | 4,5-Me$_2$ | Me | H | H | Me | 6-Me | |
| 156 | 4,5-Me$_2$ | Me | H | H | H | 3-OMe | |
| 157 | 4,5-Me$_2$ | Me | H | H | H | 3-OMe-6-Me | |
| 158 | 4-Cl-5-Me | Me | H | H | Me | 6-OMe | |
| 159 | 4-Cl-5-Me | Me | H | H | Me | 6-Me | |
| 160 | 4-Cl-5-Me | Me | H | H | H | 3-OMe | |
| 161 | 4-Cl-5-Me | Me | H | H | H | 3-OMe-6-Me | |
| 162 | 4,5-Cl$_2$ | Me | H | H | Me | 6-OMe | |
| 163 | 4,5-Cl$_2$ | Me | H | H | Me | 6-Me | |
| 164 | 4,5-Cl$_2$ | Me | H | H | H | 3-OMe | |
| 165 | 4,5-Cl$_2$ | Me | H | H | H | 3-OMe-6-Me | |
| 166 | 4,5,6-Me$_3$ | Me | H | H | Me | 6-OMe | |
| 167 | 4,5,6-Me$_3$ | Me | H | H | Me | 6-Me | |
| 168 | 4,5,6-Me$_3$ | Me | H | H | H | 3-OMe | |
| 169 | 4,5,6-Me$_3$ | Me | H | H | H | 3-OMe-6-Me | |
| 170 | 4-Cl-5,6-Me$_2$ | Me | H | H | Me | 6-OMe | |
| 171 | 4-Cl-5,6-Me$_2$ | Me | H | H | Me | 6-Me | |
| 172 | 4-Cl-5,6-Me$_2$ | Me | H | H | H | 3-OMe | |
| 173 | 4-Cl-5,6-Me$_2$ | Me | H | H | H | 3-OMe-6-Me | |
| 174 | 4,5-Cl$_2$-6-Me | Me | H | H | Me | 6-OMe | |
| 175 | 4,5-Cl$_2$-6-Me | Me | H | H | Me | 6-Me | |
| 176 | 4,5-Cl$_2$-6-Me | Me | H | H | H | 3-OMe | |
| 177 | 4,5-Cl$_2$-6-Me | Me | H | H | H | 3-OMe-6-Me | |
| 178 | 4-Me-6-Br | Me | H | H | Me | 6-OMe | |
| 179 | 4-Me-6-Br | Me | H | H | Me | 6-Me | |
| 180 | 4-Me-6-Br | Me | H | H | H | 3-OMe | |
| 181 | 4-Me-6-Br | Me | H | H | H | 3-OMe-6-Me | |
| 182 | 4-Cl-6-Br | Me | H | H | Me | 6-OMe | |
| 183 | 4-Cl-6-Br | Me | H | H | Me | 6-Me | |
| 184 | 4-Cl-6-Br | Me | H | H | H | 3-OMe | |
| 185 | 4-Cl-6-Br | Me | H | H | H | 3-OMe-6-Me | |
| 186 | 5,6-Me$_2$ | Me | H | H | Me | 6-Me | mp 103–104° C. |
| 187 | 5-Me | Me | H | H | Me | 6-OMe | mp 88–89° C. |
| 188 | 5-Cl | Me | H | H | Me | 6-OMe | mp 98–99° C. |
| 189 | 4-Me-6-Cl | Me | H | H | Me | 6-Me | mp 102–103.5° C. |
| 190 | 5-Cl-6-Me | Me | H | H | Me | 6-OMe | mp 95–98° C. |
| 191 | 3,4-Me$_2$ | Me | H | H | Me | 6-OMe | mp 125–126° C. |
| 192 | 4,6-Me$_2$ | Me | H | H | CH$_2$OMe | 4-Me | n$_D^{20.7}$ 1.5559 |
| 193 | 4-Et-6-Me | Me | H | H | Me | 6-OMe | mp 110–112° C. |
| 194 | 4,6-Me$_2$ | Me | H | H | CH$_2$OMe | 3-Me | n$_D^{20.7}$ 1.5400 |
| 195 | 4,6-Me$_2$ | Me | H | H | Me | 6-OMe | mp 114–115° C. |
| 196 | 4,6-Me$_2$ | H | H | H | Me | 6-OMe | mp 103–105° C. |
| 197 | 4,6-Me$_2$ | H | H | H | Me | 3,5-Cl$_2$-6-OMe | mp 103–105° C. |
| 198 | 4,6-Me$_2$ | Me | H | H | Me | 5,6-F$_2$ | mp 83–86° C. |
| 199 | 4,6-Me$_2$ | Me | H | H | CH$_2$OEt | 6-F | mp 64–65° C. |
| 200 | 4,6-Me$_2$ | Me | H | H | H | 6-F | mp 88–90° C. |
| 201 | 4,6-Me$_2$ | Me | H | H | Me | 3,6-F$_2$ | mp 46–47° C. |
| 202 | 4,6-Me$_2$ | Me | H | H | Me | 6-iPr | n$_D^{23.6}$ 1.5607 |
| 203 | 4,6-Me$_2$ | H | H | H | Me | 6-Me | n$_D^{22.6}$ 1.5787 |
| 204 | 4,6-Me$_2$ | H | H | H | Me | 6-F | mp 51–53° C. |
| 205 | 4,6-Me$_2$ | Me | H | H | Me | 3-F-6-NMe$_2$ | n$_D^{23.0}$ 1.5525 |
| 206 | 4,6-Me$_2$ | Me | H | H | C(O)Bu$^t$ | 3-OMe | *1 |
| 207 | 4,6-Me$_2$ | Me | H | H | C(O)Me | 3-OMe | *2 |
| 208 | 4,6-Me$_2$ | H | H | H | Me | 6-OMe-4-Me | mp 95–96° C. |
| 209 | 4,6-Me$_2$ | Me | H | H | Me | 6-OMe-4-Me | mp 94–95° C. |
| 210 | 4,6-Me$_2$ | H | H | H | Me | 6-CH=CH$_2$ | n$_D^{20.7}$ 1.5694 |
| 211 | 4,6-Me$_2$ | Me | H | H | S(O)$_2$CF$_3$ | 3-OMe | *3 |
| 212 | 4,6-Me$_2$ | Me | H | H | C(O)Me | 3,6-(OMe)$_2$ | mp 120–122° C. |
| 213 | 4,6-Me$_2$ | H | H | H | Me | 4-Cl-6-OMe | mp 132–133° C. |
| 214 | 4,6-Me$_2$ | Me | H | H | Me | 6-CN | mp 130–131° C. |
| 215 | 4,6-Me$_2$ | H | H | H | Me | 6-CN | mp 95–97° C. |
| 216 | 4,6-Me$_2$ | H | H | H | Me | 4-F-6-OMe | mp 122–123° C. |
| 217 | 4,6-Me$_2$ | H | H | H | Me | 6-NO$_2$ | mp 122–123° C. |
| 218 | 4,6-Me$_2$ | H | H | H | Me | 6-NHC(O)Me | mp 133–134° C. |
| 219 | 4-Cl-6-Me | H | H | H | Me | 6-OMe | mp 106–108° C. |
| 220 | 4-Cl-6-Me | H | H | H | Me | 6-F | mp 85–88° C. |
| 221 | 6-Cl | H | H | H | Me | 6-OMe | mp 120–122° C. |
| 222 | 4,6-Me$_2$ | H | H | H | Me | 6-NH$_2$ | mp 115–117° C. |
| 223 | 4,6-Me$_2$ | H | H | H | Me | 6-NHMe | mp 73–75° C. |

TABLE 1-continued

| No. | R¹ | R² | R³ | R⁴ | R⁵ | R⁶ | Remarks | Physical Constant |
|---|---|---|---|---|---|---|---|---|
| 224 | 4,6-Me₂ | H | H | H | Me | 6-F-4-OMe | | mp 62–64° C. |
| 225 | 4,6-Me₂ | H | H | H | Me | 6-NMe₂ | | $n_D^{20.7}$ 1.5695 |
| 226 | 4-NH₂-6-Me | H | H | H | Me | 6-OMe | | mp 166–170° C. |
| 227 | 4,6-Me₂ | H | H | H | Me | 6-OC(O)Me | *4 | |
| 228 | 6-Me | H | H | H | Me | 6-OMe | | mp 132–133° C. |
| 229 | 4-Br-6-Me | H | H | H | Me | 6-OMe | | mp 114–116° C. |
| 230 | 4-Me-6-Cl | H | H | H | Me | 6-OMe | | mp 161–163° C. |
| 231 | H | H | H | H | Me | 6-OMe | | mp 77–79° C. |
| 232 | 4-Cl | H | H | H | Me | 6-OMe | | mp 104–107° C. |
| 233 | 4,6-Me₂ | H | H | H | Me | 4,6-(OMe)₂ | | mp 125–127° C. |
| 234 | 4,6-Me₂ | H | H | H | Me | 6-Br | | mp 68–70° C. |
| 235 | 4,6-Me₂ | H | H | H | Me | 6-C≡CH | | mp 116–118° C. |
| 236 | 4,6-Me₂ | H | H | H | Me | 6-OMe | HCl salt | mp 203° C.(dec) |
| 237 | 4,6-Me₂ | H | H | H | Me | 6-CH₂OMe | | mp 67–68° C. |
| 238 | 4-Cl | H | H | H | Me | 6-F | | mp 100–103° C. |
| 239 | 4,6-Me₂ | H | Me | H | Me | 6-OMe | | mp 71–74° C. |
| 240 | 4,6-Me₂ | H | H | H | Me | 6-OMe-3-Me | | mp 84–86° C. |
| 241 | 3-OMe-6-Me | Me | H | H | Me | 6-OMe | | mp 139–140° C. |
| 242 | 4,6-Me₂ | H | H | H | Me | 3-Cl-6-OMe | | mp 80–81° C. |
| 243 | 4,6-Me₂ | Me | Me | H | Me | 6-F | | mp 103–105° C. |
| 244 | 6-Me | Et | H | H | Me | 6-OMe | | *5 |
| 245 | 4-Cl-5,6-Me₂ | H | H | H | Me | 6-OMe | | mp 148–150° C. |
| 246 | 4,6-Me₂ | H | Me | H | Me | 6-OMe | | mp 88–95° C. |
| 247 | 4,6-Me₂ | H | H | H | Me | 6-OMe | MeSO₃H salt | mp 167–168° C. |
| 248 | 4,6-Me₂ | H | H | H | Me | 6-OMe | (CO₂H)₂ salt | mp 145–147° C. |
| 249 | 4,6-Me₂ | H | H | H | Me | 5-OMe | | $n_D^{20.6}$ 1.5758 |
| 250 | 4,6-Me₂ | H | H | H | Et | 6-Me | | $n_D^{20.4}$ 1.5655 |
| 251 | 4,6-Me₂ | H | H | H | Me | 3-OMe | | $n_D^{20.3}$ 1.5615 |
| 252 | 4,6-Me₂ | H | H | H | Me | 5,6-F₂ | | mp 89–92° C. |
| 253 | 4-Cl-6-Me | H | H | H | Me | 4,6-(OMe)₂ | | mp 140–143° C. |
| 254 | 4-Cl-6-Me | H | H | H | Me | 5,6-F₂ | | mp 95–97° C. |
| 255 | 4,6-Me₂ | Me | H | H | CH₂OMe | 3-OMe | | *6 |
| 256 | 4,6-Me₂ | H | H | H | CHF₂ | 6-Me | | mp 80–82° C. |
| 257 | 4,6-Me₂ | H | H | H | CHF₂ | 6-OMe | | |
| 258 | 4,6-Me₂ | H | H | H | Me | 4,6-F₂ | | *7 |
| 259 | 4,6-Me₂ | H | H | H | Me | 3,6-F₂ | | *8 |
| 260 | 4,6-Me₂ | H | H | H | Me | 6-SMe | | *9 |
| 261 | 4-Cl-6-Me | H | H | H | Me | 6-OMe | HCl salt | mp 174–175° C. |

| No. | R¹ | R² | R³ | R⁴ | R⁵ | R⁶ | Physical Constant |
|---|---|---|---|---|---|---|---|
| 262 | 4-Cl-6-Me | H | H | H | Me | 6-Me | *10 |
| 263 | 4-Cl-6-Me | H | H | H | Me | 3,6-F₂ | *11 |
| 264 | 4-Cl-6-Me | H | H | H | Me | 6-F-4-OMe | *12 |
| 265 | 4,6-Me₂ | H | H | H | Me | 6-OEt | *13 |
| 266 | 4-Cl-6-Me | H | Me | Me | Me | 6-Me | |
| 267 | 4-Cl-6-Me | H | Me | Me | Me | 3,6-F₂ | |
| 268 | 4-Cl-6-Me | H | Me | Me | Me | 6-F-4-OMe | |
| 269 | 4,6-Me₂ | H | Me | Me | Me | 6-OMe | |
| 270 | 4,6-Me₂ | H | Me | Me | Me | 6-Me | |
| 271 | 4,6-Me₂ | cyclo-Pr | H | H | Me | 3,6-(OMe)₂ | |
| 272 | 4,6-Me₂ | cyclo-Pr | H | H | Me | 6-OMe | |
| 273 | 4,6-Me₂ | cyclo-Pr | H | H | Me | 6-Me | |
| 274 | 4-Cl-6-Me | H | H | H | cyclo-Pr | 3,6-(OMe)₂ | |
| 275 | 4-Cl-6-Me | H | H | H | cyclo-Pr | 6-OMe | |
| 276 | 4-Cl-6-Me | H | H | H | cyclo-Pr | 6-Me | |
| 277 | 4-F-6-Me | H | H | H | cyclo-Pr | 3,6-(OMe)₂ | |
| 278 | 4-F-6-Me | H | H | H | cyclo-Pr | 6-OMe | |
| 279 | 4-F-6-Me | H | H | H | cyclo-Pr | 6-Me | |
| 280 | 4-CF₃-6-Me | H | H | H | cyclo-Pr | 3,6-(OMe)₂ | |
| 281 | 4-CF₃-6-Me | H | H | H | cyclo-Pr | 6-OMe | |
| 282 | 4-CF₃-6-Me | H | H | H | cyclo-Pr | 6-Me | |
| 283 | 4,6-Me₂ | H | H | H | cyclo-Pr | 3,6-(OMe)₂ | |
| 284 | 4,6-Me₂ | H | H | H | cyclo-Pr | 6-OMe | |
| 285 | 4,6-Me₂ | H | H | H | cyclo-Pr | 6-Me | |
| 286 | 4-Cl-6-Me | H | H | H | CF₃ | 3,6-Cl₂ | |
| 287 | 4-Cl-6-Me | H | H | H | CF₃ | 3-Cl | |
| 288 | 4-Cl-6-Me | H | H | H | CF₃ | 4-Cl | |
| 289 | 4-F-6-Me | H | H | H | CH₂Cl | 3,6-(OMe)₂ | |
| 290 | 4-F-6-Me | H | H | H | CH₂Cl | 6-OMe | |
| 291 | 4-F-6-Me | H | H | H | CH₂Cl | 6-Me | |
| 292 | 4-CF₃-6-Me | H | H | H | CH₂CH₂Cl | 3,6-(OMe)₂ | |
| 293 | 4-CF₃-6-Me | H | H | H | CH₂CH₂Cl | 6-OMe | |
| 294 | 4-CF₃-6-Me | H | H | H | CH₂CH₂Cl | 6-Me | |
| 295 | 4-cyclo-Pr-6-Me | H | H | H | Me | 3,6-(OMe)₂ | |
| 296 | 4-cyclo-Pr-6-Me | H | H | H | Me | 6-OMe | |
| 297 | 4-cyclo-Pr-6-Me | H | H | H | Me | 6-Me | |

TABLE 1-continued

| | | | | | | | |
|---|---|---|---|---|---|---|---|
| 298 | 6-cyclo-Pr-4-Me | H | H | H | Me | 3,6-(OMe)$_2$ | |
| 299 | 6-cyclo-Pr-4-Me | H | H | H | Me | 6-OMe | |
| 300 | 6-cyclo-Pr-4-Me | Me | H | H | Me | 6-Me | |
| 301 | 6-CH$_2$OMe | Me | H | H | Me | 3,6-(OMe)$_2$ | |
| 302 | 6-CH$_2$OMe | Me | H | H | Me | 6-OMe | |
| 303 | 6-CH$_2$OMe | Me | H | H | Me | 6-Me | |
| 304 | 4-CF$_3$-6-Me | Me | H | H | Me | 4-cyclo-Pr-6-Me | |
| 305 | 4-CF$_3$-6-Me | Me | H | H | Me | 4-cyclo-Pr-6-OMe | |
| 306 | 4-CF$_3$-6-Me | Me | H | H | Me | 4-cyclo-Pr-6-Cl | |
| 307 | 4,6-Me$_2$ | Me | H | H | Me | 3-OH | |
| 308 | 4,6-Me$_2$ | Me | H | H | Me | 4-OH | |
| 309 | 4,6-Me$_2$ | Me | H | H | Me | 5-OH | |
| 310 | 4-Cl-6-Me | Me | H | H | Me | 3-OH | |
| 311 | 4-Cl-6-Me | Me | H | H | Me | 4-OH | |
| 312 | 4-Cl-6-Me | Me | H | H | Me | 5-OH | |
| 313 | 4-F-6-Me | Me | H | H | Me | 3-OH | |
| 314 | 4-F-6-Me | Me | H | H | Me | 4-OH | |
| 315 | 4-F-6-Me | Me | H | H | Me | 5-OH | |
| 316 | 4-CF$_3$-6-Me | Me | H | H | Me | 3-OH | |
| 317 | 4-CF$_3$-6-Me | Me | H | H | Me | 4-OH | |
| 318 | 4-CF$_3$-6-Me | Me | H | H | Me | 5-OH | |
| 319 | 4,6-Me$_2$ | Me | H | H | Me | 3-OH-6-Me | |
| 320 | 4-Cl-6-Me | Me | H | H | Me | 3-OH-6-Me | |
| 321 | 4-CF$_3$-6-Me | Me | H | H | Me | 3-OH-6-Me | |
| 322 | 4,6-Me$_2$ | Me | H | H | Me | 4-OH-6-Me | |
| 323 | 4-Cl-6-Me | Me | H | H | Me | 4-OH-6-Me | |
| 324 | 4-CF$_3$-6-Me | Me | H | H | Me | 4-OH-6-Me | |
| 325 | 4,6-Me$_2$ | Me | H | H | Me | 5-OH-6-Me | |
| 326 | 4-Cl-6-Me | Me | H | H | Me | 5-OH-6-Me | |
| 327 | 4-CF$_3$-6-Me | Me | H | H | Me | 5-OH-6-Me | |
| 328 | 4,6-Me$_2$ | Me | H | H | Me | 3-OCH$_2$OMe | |
| 329 | 4-Cl-6-Me | Me | H | H | Me | 3-OCH$_2$OMe | |
| 330 | 4-CF$_3$-6-Me | Me | H | H | Me | 3-OCH$_2$OMe | |
| 331 | 4,6-Me$_2$ | Me | H | H | Me | 4-OCH$_2$OMe | |
| 332 | 4-Cl-6-Me | Me | H | H | Me | 4-OCH$_2$OMe | |
| 333 | 4-CF$_3$-6-Me | Me | H | H | Me | 4-OCH$_2$OMe | |
| 334 | 4,6-Me$_2$ | Me | H | H | Me | 5-OCH$_2$OMe | |
| 335 | 4-Cl-6-Me | Me | H | H | Me | 5-OCH$_2$OMe | |
| 336 | 4-CF$_3$-6-Me | Me | H | H | Me | 5-OCH$_2$OMe | |
| 337 | 6-Me | Me | H | H | Me | 3-OMe | $n_{D23.5}$ 1.5696 |
| 338 | 6-Me | Me | H | H | Me | 3-Me | $n_{D23.5}$ 1.5640 |
| 339 | 6-Me | Me | H | H | Me | 5-OMe | $n_{D19.0}$ 1.5687 |
| 340 | 6-Me | Me | H | H | Me | 3-Cl | $n_{D19.1}$ 1.5679 |
| 341 | 4,6-Me$_2$ | Me | Me | H | Me | 3-OMe | *14 |
| 342 | 4,6-Me$_2$ | Me | H | H | Me | 3-OMe | $n_{D21.6}$ 1.5649 |

1H-NMR (CDCl$_3$, TMS, δ ppm) data:

* 1: 1.39 (s, 9H), 2.30 (s, 3H), 2.32 (s, 3H), 2.50 (s, 3H), 3.80 (s, 3H), 5.29 (s, 2H), 6.88–7.23 (m, 4H), 7.48 (d, 1H)
* 2: 2.30 (s, 3H), 2.32 (s, 6H), 2.51 (s, 3H), 3.84 (s, 3H), 5.22 (s, 2H), 6.91–7.26 (m, 4H), 7.48 (d, 1H)
* 3: 2.30 (s, 3H), 2.36 (s, 3H), 2.51 (s, 3H), 3.90 (s, 3H), 5.36 (s, 2H), 6.92–7.35 (m, 4H), 7.48 (d, 1H)
* 4: 2.31 (s, 3H), 2.32 (s, 3H), 2.50 (s, 3H), 3.89 (s, 3H), 5.29 (s, 2H), 6.76 (d, 1H), 6.82 (d, 1H), 6.94 (d, 1H), 7.27–7.43 (m, 2H), 8.10 (s, 1H)
* 5: 1.17 (t, 3H), 2.62 (s, 3H), 2.99 (q, 2H), 3.94 (s, 6H), 5.45 (s, 2H), 6.68 (d, 2H), 7.11–7.82 (m, 4H)
* 6: 2.31 (s, 3H), 2.36 (s , 3H), 2.51 (s, 3H), 3.62 (s, 3H), 3.86 (s, 3H), 5.16 (s, 2H), 5.40 (s, 2H), 6.86–7.13 (m, 4H), 7.51 (d, 1H)
* 7: 2.30 (s, 3H), 2.50 (s, 3H), 3.86 (s, 3H), 5.26 (s, 2H), 6.35–6.55 (m, 2H), 6.93 (d, 1H), 7.43 (d, 1H), 8.09 (s, 1H)
* 8: 2.31 (s, 3H), 2.50 (s, 3H), 3.98 (s, 3H), 5.31 (s, 2H), 6.77 (m, 1H), 6.93 (d, 1H), 7.04 (m, 1H), 7.43 (d, 1H), 8.09 (s, 1H)
* 9: 2.32 (s, 3H), 2.47 (s, 3H), 2.51 (s, 3H), 3.86 (s, 3H), 5.50 (s, 2H), 6.76 (d, 1H, J=8Hz), 6.93 (d, 1H), 6.94 (d, 1H, J=8Hz), 7.29 (t, 1H, J=8Hz), 7.49 (d, 1H), 8.13 (s, 1H)
* 10: 2.32 (s, 3H), 2.47 (s, 3H), 2.51 (s, 3H), 3.86 (s, 3H), 5.50 (s, 2H), 6.76 (d, 1H, J=8 Hz), 6.93 (d, 1H), 6.94 (d, 1H, J=8 Hz), 7.29 (t, 1H, J=8 Hz), 7.49 (d, 1H), 8.13 (s, 1H)
* 11: 2.52 (s, 3H), 4.00 (d, 3H), 5.31 (d, 2H), 6.78 (m, 1H), 7.05 (m, 1H), 7.11 (d, 1H), 7.63 (d, 1H), 8.07 (s, 1H)
* 12: 2.52 (s, 3H), 3.80 (s, 3H), 3.84 (s, 3H), 5.26 (s, 2H), 6.28 (m, 2H), 7.11 (d, 1H), 7.67 (d, 1H), 8.07 (s, 1H)
* 13: 1.40 (t, 3H), 2.32 (s, 3H), 2.51 (s, 3H), 3.85 (s, 3H), 4.08 (q, 2H), 5.40 (s, 2H), 6.58 (d, 2H), 6.94 (d, 1H), 7.27 (t, 1H), 7.48 (d, 1H), 8.12 (s, 1H)

[Fungicide]

Now, examples of carrying out the present invention will be explained. However, it should be noted that the present invention is not limited to the description in the Examples and may be modified to various modes of embodiments in the scope falling within the subject matter of the present invention. Note that the term of "part" in the Formulation Example described later denotes "part by weight".

Example 15

Wettable Powder Formulation

| A compound of present invention | 40 part |
|---|---|
| Diatomaceous earth | 53 part |
| Higher alcohol sulfate | 4 part |
| Alkylnaphthalenesulfonate | 3 part |

The above-recited components are mixed and pulverized to fine particles to thereby obtain a wettable power formulation for the. compound of the present invention with the content of 40% based on the active ingredient.

Example 16

Emulsifiable Concentrate Formulation

| A compound of present invention | 30 part |
|---|---|
| Xylene | 33 part |
| Dimethylformamide | 30 part |
| Polyoxyethylene alkyl allyl ether | 7 part |

The above-recited components are mixed and prepared to a solution to thereby obtain an emulsifiable concentrate formulation for the compound of the present invention with the. content of 30% based on the active ingredient.

Example 17

Power Formulation

| A compound of present invention | 10 part |
|---|---|
| Talc | 89 part |
| Polyoxyethylene alkyl allyl ether | 1 part |

The above-recited components are mixed and pulverized fine Particles to thereby obtain a power formulation for the compound of the present invention with the content of 10% based on the active ingredient.

Example 18

Granular Formulation

| A compound of present invention | 5 part |
|---|---|
| Clay | 73 part |
| Bentonite | 20 part |
| Dioctylsulfosuccinate sodium salt | 1 part |
| Sodium phosphate | 1 part |

The above-recited components are mixed, thoroughly grinded, added with water, then kneaded, and granulated, and further dried to thereby obtain a granular formulation for the compound of the present invention with the content of 5% based on the active ingredient.

Example 19

Suspension Concentrate Formulation

| A compound of present invention | 10 part |
|---|---|
| Sodium ligninsulfonate | 4 part |
| Sodium dodecylbenzenesulfonate | 1 part |
| Xanthane gum | 0.2 part |
| Water | 84.8 part |

The above-recited components are mixed and grinded by wet grinding to a particle size of less than 1 μm to thereby obtain a suspension concentrate for the compound of the present invention with the content of 10% based on the active ingredient.

Industrial Use of the Invention

Now, explanation is made on how the compounds according to the present invention are effective as an active ingredient of a fungicide for controlling various plant diseases with reference to Test examples described later. In the Test Examples, the control efficacy is determined by visually checking the infested state of the test plants at the time of observation, namely, checking the damage to the host plants and the developing state of the disease-causing fungus appeared on leaves, stems, etc. of the test plants, compared to the control test plants which are healthy.

Test Example 1

Test on Apple Scab Control (Preventive Application)

The emulsifiable concentrate prepared for the compound according to the present invention is diluted so as to prepared the solution at a concentration of 200 ppm, and the diluted solution was the sprayed to apple young trees (variety; Kokko, at 3–4 leaf stage) grown in an unglazed pot. The spayed solution was naturally dried, then conidia of apple scab fungus (*Venturia inaegualis*) were inoculated onto the test apples. The inoculated apple trees were placed in a room being maintained at 20° C. and high humidity with repeated lighting of 12 hours intervals, and the apple trees are allowed to stand in the room for two weeks. After that period, assessment was made to determine the control efficacy by checking the infestation degree by the fungus on the leaves in comparison with the control apple trees. As a result, the compounds having the following compound numbers showed to have excellent control performance value higher than 75% on the disease. Note that the compound numbers in the following correspond to the same compound numbers in the Table 1.

Compound Nos. 1, 3, 6, 8, 12, 14, 15, 20, 24, 25, 26, 37, 48, 49, 194, 200, 207, 210, 231, 244

Test Example 2

Test on Kidney Bean Gray Mold Control

Flowers of Kidney bean (variety; Nagauzura) grown in a flat vessel for culturing seedlings are cut, and the cut flowers were dipped into a solution prepared by diluting the emulsifiable concentrate prepared for the compound of the present invention at a concentration of 50 ppm based on the active ingredient. After the dipping, the flowers were dried at a room temperature. Then, spore solution of snap bean gray mold fungus (*Botrytis cinerea*) was sprayed to the flowers. The flowers sprayed with spores of the gray mold fungus were placed on the leaves which were detached from healthy Kidney bean plants, and those leaves were placed in a room being maintained at 20° C. and high humidity with repeated lighting of 12 hours intervals, and the Kidney bean leaves were incubated in the room for 7 days. Then, the infestation degree by the fungus on the leaves was checked in comparison to the control healthy leaves to determine the control efficacy. As a result, the compounds of the following compound numbers showed to have excellent control performance. Note that the compound numbers in the following correspond to the same compound numbers in the Table 1. Compound Nos. 1, 3, 6, 7, 11, 12, 13, 14, 15, 18, 20, 21, 22, 23, 25, 26, 27, 29, 36, 48, 49, 192, 194, 195, 196, 198, 201, 203, 204, 207, 208, 209, 210, 213, 216, 219, 220, 222, 223, 224, 225, 227, 228, 229, 231, 233, 234, 235, 236, 237, 239, 240, 242

What is claimed is:

1. An Oxime O-ether compound represented by formula (I);

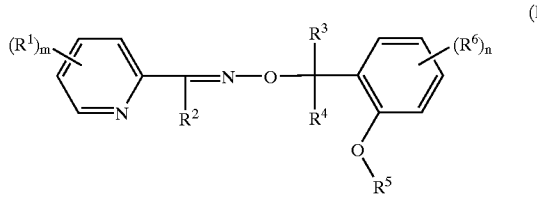

wherein

R$^1$ represents C$_{1-6}$ alkyl, C$_{3-6}$ cycloalkyl, C$_{1-6}$ alkoxy, C$_{1-6}$ alkylthio, amino, mono- or di-(C$_{1-6}$ alkyl)amino, C$_{1-6}$ acyloxy, C$_{1-6}$ alkoxy C$_{1-6}$ alkyl, C$_{1-6}$ haloalkyl, hydroxy or Halogen atom;

m represents an integer of 1 to 4, and when m is 2 or more integer, each of R$^1$ may be same or different from one to another;

R$^2$ represents hydrogen atom, C$_{1-6}$ alkyl or C$_{3-6}$ cycloalkyl;

R$^3$ and R$^4$ are same or different from one to another, and each independently represents hydrogen atom or C$_{1-6}$ alkyl;

R$^5$ represents hydrogen atom, C$_{1-6}$ alkyl, C$_{3-6}$ cycloalkyl, C$_{1-6}$ haloalkyl, C$_{1-6}$ alkoxy C$_{1-6}$ alkyl, C$_{1-6}$ alkoxy C$_{1-6}$ alkoxy C$_{1-6}$ alkyl, C$_{7-10}$ aralkyl, C$_{7-10}$ aralkyloxy C$_{1-6}$ alkyl, C$_{1-6}$ alkylcarbonyl, C$_{1-6}$ alkylsulfonyl or C$_{1-6}$ haloalkylsulfonyl;

R$^6$ represents C$_{1-6}$ alkyl, C$_{3-6}$ cycloalkyl, C$_{2-6}$ alkenyl, C$_{2-6}$ alkynyl, C$_{1-6}$ alkoxy, C$_{1-6}$ alkoxy C$_{1-6}$ alkoxy, C$_{1-6}$ alkylcarbonyloxy, C$_{1-6}$ alkoxy C$_{1-6}$ alkyl, C$_{1-6}$ haloalkyl, cyano, nitro, amino, mono- or di-(C$_{1-6}$ alkyl) amino, C$_{1-6}$ alkylcarbonylamino, C$_{1-6}$ alkylthio, hydroxy or Halogen atom; and n represents an integer of 1 to 4, and when n is 2 or more, each of R$^6$ may be same or different from one to another.

2. An Oxime O-ether compound represented by formula (I')

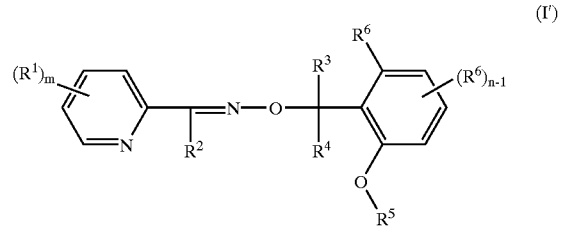

wherein

R$^1$ represents C$_{1-6}$ alkyl, C$_{3-6}$ cycloalkyl, C$_{1-6}$ alkoxy, C$_{1-6}$ alkylthio, amino, mono- or di-(C$_{1-6}$ alkyl)amino, C$_{1-6}$ acyloxy, C$_{1-6}$ alkoxy C$_{1-6}$ alkyl, C$_{1-6}$ haloalkyl, hydroxy or Halogen atom;

m represents an integer of 1 to 4, and when m is 2 or more integer, each of R$^1$ may be same or different from one to another;

R$^2$ represents hydrogen atom, C$_{1-6}$ alkyl or C$_{3-6}$ cycloalkyl;

R$^3$ and R$^4$ are same or different from one to another, and each independently represents hydrogen atom or C$_{1-6}$ alkyl;

R$^5$ represents hydrogen atom, C$_{1-6}$ alkyl, C$_{3-6}$ cycloalkyl, C$_{1-6}$ haloalkyl, C$_{1-6}$ alkoxy C$_{1-6}$ alkyl, C$_{1-6}$ alkoxy C$_{1-6}$ alkoxy C$_{1-6}$ alkyl, C$_{7-10}$ aralkyl, C$_{7-10}$ aralkyloxy C$_{1-6}$ alkyl, C$_{1-6}$ alkylcarbonyl, C$_{1-6}$ alkylsulfonyl or C$_{1-6}$ haloalkylsulfonyl;

R$^6$ represents C$_{1-6}$ alkyl, C$_{3-6}$ cycloalkyl, C$_{2-6}$ alkenyl, C$_{2-6}$ alkynyl, C$_{1-6}$ alkoxy, C$_{1-6}$ alkoxy C$_{1-6}$ alkoxy, C$_{1-6}$ alkylcarbonyloxy, C$_{1-6}$ alkoxy C$_{1-6}$ alkyl, C$_{1-6}$ haloalkyl, cyano, nitro, amino, mono- or di-(C$_{1-6}$ alkyl) amino, C$_{1-6}$ alkylcarbonylamino, C$_{1-6}$ alkylthio, hydroxy or Halogen atom; and n represents an integer of 1 to 4, and when n is 2 or more, each of R$^6$ may be same or different from one to another.

3. A fungicidal composition for agricultural and horticultural use characterized by comprising one or more of an oxime O-ether compound represented by formula (I)

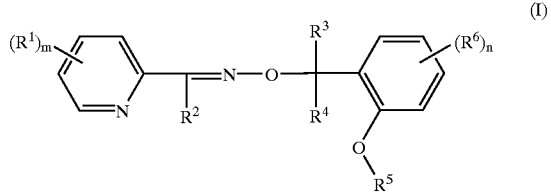

wherein

R$^1$ represents C$_{1-6}$ alkyl, C$_{3-6}$ cycloalkyl, C$_{1-6}$ alkoxy, C$_{1-6}$ alkylthio, amino, mono- or di-(C$_{1-6}$ alkyl)amino, C$_{1-6}$ acyloxy, C$_{1-6}$ alkoxy C$_{1-6}$ alkyl, C$_{1-6}$ haloalkyl, hydroxy or Halogen atom;

m represents an integer of 1 to 4, and when m is 2 or more integer, each of R$^1$ may be same or different from one to another;

R$^2$ represents hydrogen atom, C$_{1-6}$ alkyl or C$_{3-6}$ cycloalkyl;

R$^3$ and R$^4$ are same or different from one to another, and each independently represents hydrogen atom or C$_{1-6}$ alkyl;

$R^5$ represents hydrogen atom, $C_{1-6}$ alkyl, $C_{3-6}$ cycloalkyl, $C_{1-6}$ haloalkyl, $C_{1-6}$ alkoxy $C_{1-6}$ alkyl, $C_{1-6}$ alkoxy $C_{1-6}$ alkoxy $C_{1-6}$ alkyl, $C_{7-10}$ aralkyl, $C_{7-10}$ aralkyloxy $C_{1-6}$ alkyl, $C_{1-6}$ alkylcarbonyl, $C_{1-6}$ alkylsulfonyl or $C_{1-6}$ haloalkylsulfonyl;

$R^6$ represents $C_{1-6}$ alkyl, $C_{3-6}$ cycloalkyl, $C_{2-6}$ alkenyl, $C_{2-6}$ alkynyl, $C_{1-6}$ alkoxy, $C_{1-6}$ alkoxy $C_{1-6}$ alkoxy, $C_{1-6}$ alkylcarbonyloxy, $C_{1-6}$ alkoxy $C_{1-6}$ alkyl, $C_{1-6}$ haloalkyl, cyano, nitro, amino, mono- or di-($C_{1-6}$ alkyl)amino, $C_{1-6}$ alkylcarbonylamino, $C_{1-6}$ alkylthio, hydroxy or Halogen atom; and n represents an integer of 1 to 4, and when n is 2 or more, each of $R^6$ may be same or different from one to another, or the salts thereof as the active ingredient.

4. A fungicidal composition, characterized in that the active ingredient is a compound represented by the formula (I')

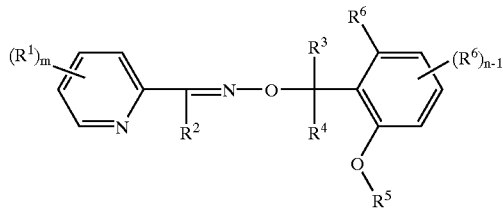

wherein $R^1$ represents $C_{1-6}$ alkyl, $C_{3-6}$ cycloalkyl, $C_{1-6}$ alkoxy, $C_{1-6}$ alkylthio, amino, mono- or di-($C_{1-6}$ alkyl)amino, $C_{1-6}$ acyloxy, $C_{1-6}$ alkoxy $C_{1-6}$ alkyl, $C_{1-6}$ haloalkyl, hydroxy or Halogen atom;

m represents an integer of 1 to 4, and when m is 2 or more integer, each of $R^1$ may be same or different from one to another;

$R^2$ represents hydrogen atom, $C_{1-6}$ alkyl or $C_{3-6}$ cycloalkyl;

$R^3$ and $R^4$ are same or different from one to another, and each independently represents hydrogen atom or $C_{1-6}$ alkyl;

$R^5$ represents hydrogen atom, $C_{1-6}$ alkyl, $C_{3-6}$ cycloalkyl, $C_{1-6}$ haloalkyl, $C_{1-6}$ alkoxy $C_{1-6}$ alkyl, $C_{1-6}$ alkoxy $C_{1-6}$ alkoxy $C_{1-6}$ alkyl, $C_{7-10}$ aralkyl, $C_{7-10}$ aralkyloxy $C_{1-6}$ alkyl, $C_{1-6}$ alkylcarbonyl, $C_{1-6}$ alkylsulfonyl or $C_{1-6}$ haloalkylsulfonyl;

$R^6$ represents $C_{1-6}$ alkyl, $C_{3-6}$ cycloalkyl, $C_{2-6}$ alkenyl, $C_{2-6}$ alkynyl, $C_{1-6}$ alkoxy, $C_{1-6}$ alkoxy $C_{1-6}$ alkoxy, $C_{1-6}$ alkylcarbonyloxy, $C_{1-6}$ alkoxy $C_{1-6}$ alkyl, $C_{1-6}$ haloalkyl, cyano, nitro, amino, mono- or di-($C_{1-6}$ alkyl)amino, $C_{1-6}$ alkylcarbonylamino, $C_{1-6}$ alkylthio, hydroxy or Halogen atom; and n represents an integer of 1 to 4, and when n is 2 or more, each of $R^6$ may be same or different from one to another.

* * * * *

UNITED STATES PATENT AND TRADEMARK OFFICE
CERTIFICATE OF CORRECTION

PATENT NO.  : 6,589,967 B1
DATED       : July 8, 2003
INVENTOR(S) : Sano et al.

It is certified that error appears in the above-identified patent and that said Letters Patent is hereby corrected as shown below:

Column 2,
Line 35, remove "Halogeno" and replace with -- Halogen --

Column 3,
Line 2, remove "Halogeno atom atom atom" and replace with -- Halogen atom --

Column 18, remove formula:

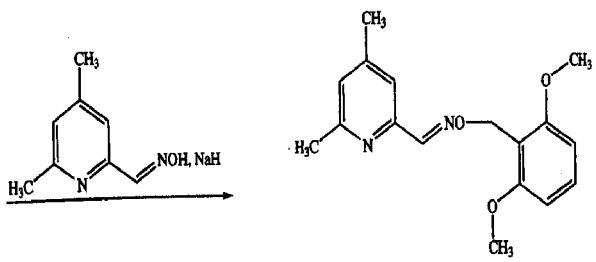

and replace with

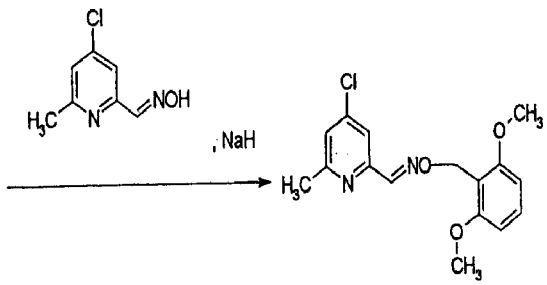

Signed and Sealed this

Seventh Day of October, 2003

JAMES E. ROGAN
*Director of the United States Patent and Trademark Office*